United States Patent
Lanar et al.

(10) Patent No.: US 7,550,275 B2
(45) Date of Patent: Jun. 23, 2009

(54) **EXPRESSION, PURIFICATION AND USES OF A *PLASMODIUM FALCIPARUM* LIVER STAGE ANTIGEN 1 POLYPEPTIDE**

(75) Inventors: David E. Lanar, Takoma Park, MD (US); Collette J. Hillier, Concord (AU); Jeffrey A. Lyon, Accident, MD (US); Evelina Angov, Bethesda, MD (US); Sanjai Kumar, Gaithersburg, MD (US); William Rogers, Jakata (ID); Arnoldo Barbosa, Tolima (CO)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 814 days.

(21) Appl. No.: 10/706,435

(22) Filed: Nov. 12, 2003

(65) Prior Publication Data

US 2006/0088547 A1  Apr. 27, 2006

Related U.S. Application Data

(60) Provisional application No. 60/425,719, filed on Nov. 12, 2002.

(51) Int. Cl.
*C12N 15/00* (2006.01)
*A61K 39/015* (2006.01)
*C07K 14/445* (2006.01)

(52) U.S. Cl. .................... 435/69.1; 435/7.1; 424/191.1; 530/350

(58) Field of Classification Search ........................ None
See application file for complete search history.

(56) References Cited

U.S. PATENT DOCUMENTS 6,319,502 B1  11/2001  Guerin-Marchand et al.

OTHER PUBLICATIONS

Phillips, Clinical Microbiol. Rev., Jan. 2001, vol. 14, No. 1, pp. 208-226.*
Giles, "Why don't we have a malaria vaccine?", http://malaria.wellcome.ac.uk/doc, Wellcome Trust malaria website, Feb. 17, 2007.*
Londono et al., J. Immunol., vol. 145, pp. 1557-1563, Sep. 1, 1990.*
Druilhe et al., PLoS Medicine, 2, 11, 1135-1145, 2005.*
Fidock et al., 1994. Plasmodium falciparum liver stage antigen-1 is well conserved and contains potent B and T cell determinants. J. Immunol. 153, 190-204.
Doolan et al., 2000. The complexity of protective immunity against liver-stage malaria. J. Immunol. 165, 1453-1462.
Connelly et al., 1997. T-Cell immunity to peptide epitopes of liver-stage antigen 1 in an area of Papua New Guinea in which malaria is holoendemic. Infect. Immunity 65, 5082-5087.
Krzych et al., 1995. T lymphocytes from volunteers immunized with irradiated Plasmodium falciparum sporozoites recognized liver and blood stage malaria antigens. J. Immunol. 155, 4072-4077.

* cited by examiner

*Primary Examiner*—Nancy Vogel
(74) *Attorney, Agent, or Firm*—Elizabeth Arwine

(57) ABSTRACT

In this application is described the expression and purification of a recombinant *Plasmodium falciparum* (3D7) LSA-NRC polypeptide. The method of the present invention produces a highly purified polypeptide which is useful as a vaccine and as a diagnostic reagent.

17 Claims, 9 Drawing Sheets

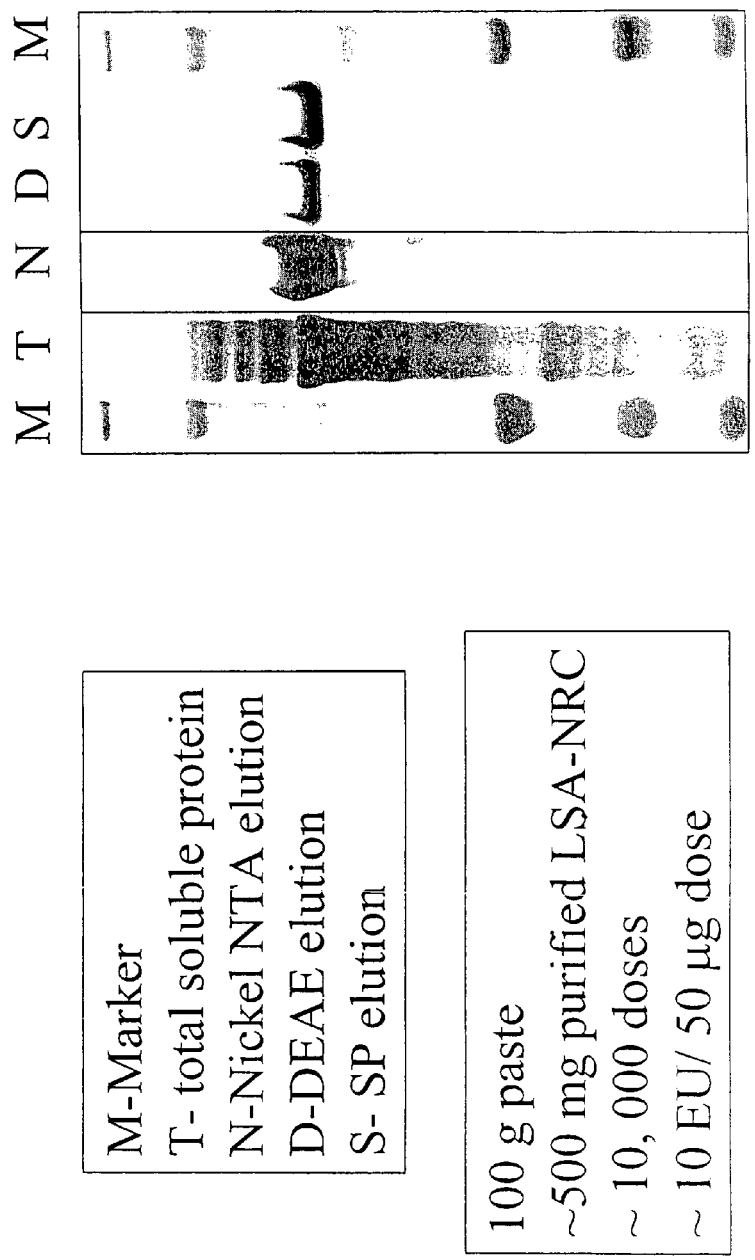
FIGURE 1

Recognition of *P. falciparum*-infected Hepatocytes

HC04 cells, 7-8 days post-infection with NF54 *P. falciparum*, Immune rabbit serum at 1:200

Recognition of LSA-NRC^MutR by Pool of Kenyan Serum by Western Blot

1. SDS PAGE
2. Naïve Human Serum
3. Kenyan Serum (ELISA titer = 1500)

FIGURE 9

SEQUENCE LISTING

<160> NUMBER OF SEQ ID NOS: 28

<210> SEQ ID NO 1
<211> LENGTH: 17
<212> TYPE: PRT
<213> ORGANISM: P. falciparum LSA-1
<220> FEATURE:
<223> OTHER INFORMATION: LSA-1 major 17 amino acid repeat

<400> SEQUENCE: 1

Glu Gln Gln Ser Asp Leu Glu Gln Glu Arg
                 5                  10

Leu Ala Lys Glu Lys Leu Gln
         15

<210> SEQ ID NO 2
<211> LENGTH: 17
<212> TYPE: PRT
<213> ORGANISM: P. falciparum LSA-1
<220> FEATURE:
<223> OTHER INFORMATION: LSA-1 minor 17 amino acid repeat

<400> SEQUENCE: 2

Glu Gln Gln Arg Asp Leu Glu Gln Glu Arg
                5                  10

Leu Ala Lys Glu Lys Leu Gln
            15

<210> SEQ ID NO 3
<211> LENGTH: 1374
<212> TYPE: DNA
<213> ORGANISM: Artificial sequence
<220> FEATURE:
<223> OTHER INFORMATION: LSA-NRC(H)Mut

<400> SEQUENCE: 3

| | |
|---|---|
| atgggtacca acagcgaaaa agacgaaatt atcaaaagca | 40 |
| atctccgctc cggcagctcc aacagccgca accgcatcaa | 80 |
| cgaggaaaag catgagaaga acatgtgct gagccacaac | 120 |
| tcctacgaga agactaaaaa caacgaaaac aacaaattct | 160 |
| ttgacaagga caaagagctg acgatgagca acgttaaaaa | 200 |
| cgtatcccag accaacttta atccctcct gcgcaacctc | 240 |
| ggcgtttccg agaacatctt tctcaaagaa acaaactga | 280 |
| acaaggaagg caaactgatt gaacatatca tcaacgacga | 320 |
| cgatgacaaa aaaaaataca ttaaaggcca ggatgaaaat | 360 |
| cgccaggaag acctcgaaga aaaagctgct gaacagcagt | 400 |
| cggacctgga acaggagcgc ctcgctaaag aaaagctcca | 440 |
| ggagcgcctc gctaaagaaa agctccagga gcaacagcgc | 480 |
| gacctggaac agcgcaaggc tgacacgaaa aaaaacctgg | 520 |
| aacgcaaaaa ggaacacggc gacgttctgg ctgaggacct | 560 |
| gtacggccgc ctggaaatcc agctatcga actcccatcc | 600 |
| gaaaacgaac gcggctacta catcccacac cagagcagcc | 640 |
| tgccacaaga taatcgcggg aactcccgcg acagtaagga | 680 |
| aatcagcatc atcgaaaaaa ccaaccgcga aagcattacc | 720 |
| accaacgtgg aaggccgccg cgacatccac aaaggccacc | 760 |
| tcgaagaaaa gaaagacggc tccatcaaac cagaacagaa | 800 |
| agaagacaaa agcgctgata ccagaaccca caccctggag | 840 |
| accgtgaaca ttagcgacgt gaacgacttc cagatcagca | 880 |
| agtacgagga cgaaatctcc gctgaatacg atgactccct | 920 |
| gatcgacgaa gaagaagacg acgaagatct ggatgaattc | 960 |
| aaaccaattg tccagtacga taactttcag gacgaagaaa | 1000 |
| atatcggcat ttacaaagaa ctcgaagacc tcatcgagaa | 1040 |
| aaacgaaaac ctggacgacc tggacgaagg catcgaaaaa | 1080 |

-continued

| | |
|---|---|
| tcctccgaag aactgagcga agaaaaaatc aaaaaaggca | 1120 |
| agaaatacga aaaaccaag gacaacaact tcaaaccaaa | 1160 |
| cgacaaatcc ctctacgacg agcacattaa aaaatacaaa | 1200 |
| aacgacaagc aagtgaacaa ggaaaaggaa aaatttatca | 1240 |
| aatccctctt ccacatcttc gatggcgata acgaaattct | 1280 |
| gcaaattgta gacgaacggt tgagcgaaga catcactaaa | 1320 |
| tacttcatga agcttggggg ctccggttct ccacaccacc | 1360 |
| accaccacca ctga | 1374 |

<210> SEQ ID NO 4
<211> LENGTH: 457
<212> TYPE: PRT
<213> ORGANISM: Artificial sequence
<220> FEATURE:
<223> OTHER INFORMATION: LSA-NRC(H)Mut

<400> SEQUENCE: 4

Met Gly Thr Asn Ser Glu Lys Asp Glu Ile
             5                    10

Ile Lys Ser Asn Leu Arg Ser Gly Ser Ser
             15                   20

Asn Ser Arg Asn Arg Ile Asn Glu Glu Lys
             25                   30

His Glu Lys Lys His Val Leu Ser His Asn
             35                   40

Ser Tyr Glu Lys Thr Lys Asn Asn Glu Asn
             45                   50

Asn Lys Phe Phe Asp Lys Asp Lys Glu Leu
             55                   60

Thr Met Ser Asn Val Lys Asn Val Ser Gln
             65                   70

Thr Asn Phe Lys Ser Leu Leu Arg Asn Leu
             75                   80

Gly Val Ser Glu Asn Ile Phe Leu Lys Glu
             85                   90

Asn Lys Leu Asn Lys Glu Gly Lys Leu Ile
             95                  100

Glu His Ile Ile Asn Asp Asp Asp Asp Lys
             105                110

Lys Lys Tyr Ile Lys Gly Gln Asp Glu Asn
             115                120

Arg Gln Glu Asp Leu Glu Glu Lys Ala Ala
             125                130

Glu Gln Gln Ser Asp Leu Glu Gln Glu Arg
             135                140

Leu Ala Lys Glu Lys Leu Gln Glu Arg Leu
             145                150

Ala Lys Glu Lys Leu Gln Glu Gln Gln Arg
             155                160

Asp Leu Glu Gln Arg Lys Ala Asp Thr Lys
             165                170

Lys Asn Leu Glu Arg Lys Lys Glu His Gly
             175                180

```
Asp Val Leu Ala Glu Asp Leu Tyr Gly Arg
            185                 190

Leu Glu Ile Pro Ala Ile Glu Leu Pro Ser
            195                 200

Glu Asn Glu Arg Gly Tyr Tyr Ile Pro His
            205                 210

Gln Ser Ser Leu Pro Gln Asp Asn Arg Gly
            215                 220

Asn Ser Arg Asp Ser Lys Glu Ile Ser Ile
            225                 230

Ile Glu Lys Thr Asn Arg Glu Ser Ile Thr
            235                 240

Thr Asn Val Glu Gly Arg Arg Asp Ile His
            245                 250

Lys Gly His Leu Glu Glu Lys Lys Asp Gly
            255                 260

Ser Ile Lys Pro Glu Gln Lys Glu Asp Lys
            265                 270

Ser Ala Asp Ile Gln Asn His Thr Leu Glu
            275                 280

Thr Val Asn Ile Ser Asp Val Asn Asp Phe
            285                 290

Gln Ile Ser Lys Tyr Glu Asp Glu Ile Ser
            295                 300

Ala Glu Tyr Asp Asp Ser Leu Ile Asp Glu
            305                 310

Glu Glu Asp Asp Glu Asp Leu Asp Glu Phe
            315                 320

Lys Pro Ile Val Gln Tyr Asp Asn Phe Gln
            325                 330

Asp Glu Glu Asn Ile Gly Ile Tyr Lys Glu
            335                 340

Leu Glu Asp Leu Ile Glu Lys Asn Glu Asn
            345                 350

Leu Asp Asp Leu Asp Glu Gly Ile Glu Lys
            355                 360

Ser Ser Glu Glu Leu Ser Glu Glu Lys Ile
            365                 370

Lys Lys Gly Lys Lys Tyr Glu Lys Thr Lys
            375                 380

Asp Asn Asn Phe Lys Pro Asn Asp Lys Ser
            385                 390

Leu Tyr Asp Glu His Ile Lys Lys Tyr Lys
            395                 400

Asn Asp Lys Gln Val Asn Lys Glu Lys Glu
            405                 410

Lys Phe Ile Lys Ser Leu Phe His Ile Phe
            415                 420

Asp Gly Asp Asn Glu Ile Leu Gln Ile Val
            425                 430

Asp Glu Arg Leu Ser Glu Asp Ile Thr Lys
            435                 440
```

```
Tyr Phe Met Lys Leu Gly Gly Ser Gly Ser
            445                 450

Pro His His His His His
            455

<210> SEQ ID NO 5
<211> LENGTH: 17
<212> TYPE: PRT
<213> ORGANISM: Artificial sequence
<220> FEATURE:
<223> OTHER INFORMATION: LSA-1 Consensus sequence of 17 amino acid
      repeats where Xaa at position 1 is either Glu or Gly; Xaa at
      position 4 is Ser or Arg; Xaa at position 6 is Asp or Ser;
      Xaa at position 9 is Glu or Asp; Xaa at position 11 is Leu
<220> FEATURE:
<223> OTHER INFORMATION: or Arg; Xaa at position 13 is Lys or Asn and
      Xaa at position 15 is Lys or Thr or Arg.

<400> SEQUENCE: 5

Xaa Gln Gln Xaa Asp Xaa Glu Gln Xaa Arg
                5                   10

Xaa Ala Xaa Glu Xaa Leu Gln
            15

<210> SEQ ID NO 6
<211> LENGTH: 24
<212> TYPE: PRT
<213> ORGANISM: P. falciparum LSA-1
<220> FEATURE:
<223> OTHER INFORMATION: P. falciparum LSA-1 T1 epitope

<400> SEQUENCE: 6

Leu Thr Met Ser Asn Val Lys Asn Val Ser
                5                   10

Gln Thr Asn Phe Lys Ser Leu Leu Arg Asn
            15                  20

Leu Gly Val Ser

<210> SEQ ID NO 7
<211> LENGTH: 17
<212> TYPE: PRT
<213> ORGANISM: P. falciparum LSA-1
<220> FEATURE:
<223> OTHER INFORMATION: P. falciparum LSA-1 LSA-Rep epitope

<400> SEQUENCE: 7

Glu Gln Gln Ser Asp Leu Glu Gln Glu Arg
                5                   10

Leu Ala Lys Glu Lys Leu Gln
            15

<210> SEQ ID NO 8
<211> LENGTH: 17
<212> TYPE: PRT
<213> ORGANISM: P. falciparum LSA-1
<220> FEATURE:
<223> OTHER INFORMATION: P. falciparum LSA-1 J epitope

<400> SEQUENCE: 8

Glu Arg Leu Ala Lys Glu Lys Leu Gln Glu
                5                   10

Gln Gln Arg Asp Leu Glu Gln
            15
```

```
<210> SEQ ID NO 9
<211> LENGTH: 20
<212> TYPE: PRT
<213> ORGANISM: P. falciparum LSA-1
<220> FEATURE:
<223> OTHER INFORMATION: P. falciparum LSA-1 NR epitope

<400> SEQUENCE: 9

Thr Lys Lys Asn Leu Glu Arg Lys Lys Glu
                 5                  10

His Gly Asp Val Leu Ala Glu Asp Leu Tyr
                15                  20

<210> SEQ ID NO 10
<211> LENGTH: 34
<212> TYPE: PRT
<213> ORGANISM: P. falciparum LSA-1
<220> FEATURE:
<223> OTHER INFORMATION: P. falciparum LSA-1 LSA-Ter epitope

<400> SEQUENCE: 10

Asn Ser Arg Asp Ser Lys Glu Ile Ser Ile
                 5                  10

Ile Glu Lys Thr Asn Arg Glu Ser Ile Thr
                15                  20

Thr Asn Val Glu Gly Arg Arg Asp Ile His
                25                  30

Lys Gly His Leu

<210> SEQ ID NO 11
<211> LENGTH: 9
<212> TYPE: PRT
<213> ORGANISM: P. falciparum LSA-1
<220> FEATURE:
<223> OTHER INFORMATION: P. falciparum LSA-1 ls6 epitope

<400> SEQUENCE: 11

Lys Pro Ile Val Gln Tyr Asp Asn Phe
                 5

<210> SEQ ID NO 12
<211> LENGTH: 23
<212> TYPE: PRT
<213> ORGANISM: P. falciparum LSA-1
<220> FEATURE:
<223> OTHER INFORMATION: P. falciparum LSA-1 T3 epitope

<400> SEQUENCE: 12

Asn Glu Asn Leu Asp Asp Leu Asp Glu Gly
                 5                  10

Ile Glu Lys Ser Ser Glu Glu Leu Ser Glu
                15                  20

Glu Lys Ile

<210> SEQ ID NO 13
<211> LENGTH: 7
<212> TYPE: PRT
<213> ORGANISM: P. falciparum LSA-1
<220> FEATURE:
<223> OTHER INFORMATION: P. falciparum LSA-1 ls8 epitope
```

-continued

```
<400> SEQUENCE: 13

Lys Pro Asn Asp Lys Ser Leu
                5

<210> SEQ ID NO 14
<211> LENGTH: 22
<212> TYPE: PRT
<213> ORGANISM: P. falciparum LSA-1
<220> FEATURE:
<223> OTHER INFORMATION: P. falciparum LSA-1 T5 epitope

<400> SEQUENCE: 14

Asp Asn Glu Ile Leu Gln Ile Val Asp Glu
                5                  10

Leu Ser Glu Asp Ile Thr Lys Tyr Phe Met
                15                 20

Lys Leu

<210> SEQ ID NO 15
<211> LENGTH: 23
<212> TYPE: PRT
<213> ORGANISM: P. falciparum LSA-1
<220> FEATURE:
<223> OTHER INFORMATION: P. falciparum LSA-1 T5-MutR epitope

<400> SEQUENCE: 15

Asp Asn Glu Ile Leu Gln Ile Val Asp Glu
                5                  10

Arg Leu Ser Glu Asp Ile Thr Lys Tyr Phe
                15                 20

Met Lys Leu

<210> SEQ ID NO 16
<211> LENGTH: 24
<212> TYPE: PRT
<213> ORGANISM: P. falciparum LSA-1
<220> FEATURE:
<223> OTHER INFORMATION: P. falciparum LSA-1 LSA1.1 epitope

<400> SEQUENCE: 16

Leu Thr Met Ser Asn Val Lys Asn Val Ser
                5                  10

Gln Thr Asn Phe Lys Ser Leu Leu Arg Asn
                15                 20

Leu Gly Val Ser

<210> SEQ ID NO 17
<211> LENGTH: 20
<212> TYPE: PRT
<213> ORGANISM: P. falciparum LSA-1
<220> FEATURE:
<223> OTHER INFORMATION: P. falciparum LSA-1 LSA1.2 epitope

<400> SEQUENCE: 17

His Thr Leu Glu Thr Val Asn Ile Ser Asp
                5                  10

Val Asn Asp Phe Gln Ile Ser Lys Tyr Glu
                15                 20
```

```
<210> SEQ ID NO 18
<211> LENGTH: 18
<212> TYPE: PRT
<213> ORGANISM: P. falciparum LSA-1
<220> FEATURE:
<223> OTHER INFORMATION: P. falciparum LSA-1.3 epitope

<400> SEQUENCE: 18

Asp Glu Asp Leu Asp Glu Phe Lys Pro Ile
                5                   10

Val Gln Tyr Asp Asn Phe Gln Asp
                15

<210> SEQ ID NO 19
<211> LENGTH: 13
<212> TYPE: PRT
<213> ORGANISM: P. falciparum LSA-1
<220> FEATURE:
<223> OTHER INFORMATION: P. falciparum LSA-1 LSA1.4 epitope

<400> SEQUENCE: 19

Ile Gly Ile Tyr Lys Glu Leu Glu Asp Leu
                5                   10

Ile Glu Lys

<210> SEQ ID NO 20
<211> LENGTH: 23
<212> TYPE: PRT
<213> ORGANISM: P. falciparum LSA-1
<220> FEATURE:
<223> OTHER INFORMATION: P. falciparum LSA-1 LSA1.5 epitope

<400> SEQUENCE: 20

Asn Glu Asn Leu Asp Asp Leu Asp Glu Gly
                5                   10

Ile Glu Lys Ser Ser Glu Glu Leu Ser Glu
                15                  20

Glu Lys Ile

<210> SEQ ID NO 21
<211> LENGTH: 15
<212> TYPE: PRT
<213> ORGANISM: P. falciparum LSA-1
<220> FEATURE:
<223> OTHER INFORMATION: P. falciparum LSA-1 LSA1.6 epitope

<400> SEQUENCE: 21

Ile Lys Lys Gly Lys Lys Tyr Glu Lys Thr
                5                   10

Lys Asp Asn Asn Phe
                15

<210> SEQ ID NO 22
<211> LENGTH: 22
<212> TYPE: PRT
<213> ORGANISM: P. falciparum LSA-1
<220> FEATURE:
<223> OTHER INFORMATION: P. falciparum LSA-1 LSA1.1 epitope

<400> SEQUENCE: 22

Asp Asn Glu Ile Leu Gln Ile Val Asp Glu
                5                   10
```

```
Leu Ser Glu Asp Ile Thr Lys Tyr Phe Met
            15                  20

Lys Leu

<210> SEQ ID NO 23
<211> LENGTH: 9
<212> TYPE: PRT
<213> ORGANISM: P. falciparum LSA-1
<220> FEATURE:
<223> OTHER INFORMATION: P. falciparum LSA-1 Doolan 1671 epitope

<400> SEQUENCE: 23

Tyr Tyr Ile Pro His Gln Ser Ser Leu
              5

<210> SEQ ID NO 24
<211> LENGTH: 34
<212> TYPE: PRT
<213> ORGANISM: P. falciparum LSA-1
<220> FEATURE:
<223> OTHER INFORMATION: Amino acid sequence of LSA-NRC(H) repeat
      sequence between N & C terminals

<400> SEQUENCE: 24

Glu Gln Gln Ser Asp Leu Glu Gln Glu Arg
             5                  10

Leu Ala Lys Glu Lys Leu Gln Glu Arg Leu
            15                  20

Ala Lys Glu Lys Leu Gln Glu Gln Gln Arg
            25                  30

Asp Leu Glu Gln

<210> SEQ ID NO 25
<211> LENGTH: 1371
<212> TYPE: DNA
<213> ORGANISM: Artificial sequence
<220> FEATURE:
<223> OTHER INFORMATION: DNA sequence of the gene LSA-NRC(H)

<400> SEQUENCE: 25
atgggtacca acagcgaaaa agacgaaatt atcaaaagca              40
atctccgctc cggcagctcc aacagccgca accgcatcaa              80
cgaggaaaag catgagaaga acatgtgct gagccacaac              120 tcctacgaga agactaaaaa caacgaaaac aacaaattct              160
ttgacaagga caaagagctg acgatgagca acgttaaaaa              200
cgtatcccag accaacttta atccctcct gcgcaacctc               240 ggcgtttccg agaacatctt tctcaaagaa aacaaactga              280
acaaggaagg caaactgatt gaacatatca tcaacgacga              320
cgatgacaaa aaaaaataca ttaaaggcca ggatgaaaat              360
cgccaggaag acctcgaaga aaaagctgct gaacagcagt              400
cggacctgga acaggagcgc ctcgctaaag aaaagctcca              440
ggagcgcctc gctaaagaaa agctccagga gcaacagcgc              480
gacctggaac agcgcaaggc tgacacgaaa aaaaacctgg              520
aacgcaaaaa ggaacacggc gacgttctgg ctgaggacct              560
gtacggccgc ctggaaatcc cagctatcga actcccatcc              600
```

-continued

| | |
|---|---|
| gaaaacgaac gcggctacta catcccacac cagagcagcc | 640 |
| tgccacaaga taatcgcggg aactcccgcg acagtaagga | 680 |
| aatcagcatc atcgaaaaaa ccaaccgcga aagcattacc | 720 |
| accaacgtgg aaggccgccg cgacatccac aaaggccacc | 760 |
| tcgaagaaaa gaaagacggc tccatcaaac cagaacagaa | 800 |
| agaagacaaa agcgctgata tccagaacca cccctggag | 840 |
| accgtgaaca ttagcgacgt gaacgacttc cagatcagca | 880 |
| agtacgagga cgaaatctcc gctgaatacg atgactccct | 920 |
| gatcgacgaa gaagaagacg acgaagatct ggatgaattc | 960 |
| aaaccaattg tccagtacga taactttcag gacgaagaaa | 1000 |
| atatcggcat ttacaaagaa ctcgaagacc tcatcgagaa | 1040 |
| aaacgaaaac ctggacgacc tggacgaagg catcgaaaaa | 1080 |
| tcctccgaag aactgagcga agaaaaaatc aaaaaaggca | 1120 |
| agaaatacga aaaaccaag gacaacaact tcaaaccaaa | 1160 |
| cgacaaatcc ctctacgacg agcacattaa aaaatacaaa | 1200 |
| aacgacaagc aagtgaacaa ggaaaaggaa aaatttatca | 1240 |
| aatccctctt ccacatcttc gatggcgata acgaaattct | 1280 |
| gcaaattgta gacgaactga gcgaagacat cactaaatac | 1320 |
| ttcatgaagc ttgggggctc cggttctcca caccaccacc | 1360 |
| accaccactg a | 1371 |

<210> SEQ ID NO 26
<211> LENGTH: 456
<212> TYPE: PRT
<213> ORGANISM: Artificial sequence
<220> FEATURE:
<223> OTHER INFORMATION: LSA-NRC(H) protein

<400> SEQUENCE: 26

Met Gly Thr Asn Ser Glu Lys Asp Glu Ile
                5                   10

Ile Lys Ser Asn Leu Arg Ser Gly Ser Ser
                15                  20

Asn Ser Arg Asn Arg Ile Asn Glu Glu Lys
                25                  30

His Glu Lys Lys His Val Leu Ser His Asn
                35                  40

Ser Tyr Glu Lys Thr Lys Asn Asn Glu Asn
                45                  50

Asn Lys Phe Phe Asp Lys Asp Lys Glu Leu
                55                  60

Thr Met Ser Asn Val Lys Asn Val Ser Gln
                65                  70

Thr Asn Phe Lys Ser Leu Leu Arg Asn Leu
                75                  80

Gly Val Ser Glu Asn Ile Phe Leu Lys Glu
                85                  90

Asn Lys Leu Asn Lys Glu Gly Lys Leu Ile
                95                  100

```
Glu His Ile Ile Asn Asp Asp Asp Lys
             105                 110

Lys Lys Tyr Ile Lys Gly Gln Asp Glu Asn
             115                 120

Arg Gln Glu Asp Leu Glu Glu Lys Ala Ala
             125                 130

Glu Gln Gln Ser Asp Leu Glu Gln Glu Arg
             135                 140

Leu Ala Lys Glu Lys Leu Gln Glu Arg Leu
             145                 150

Ala Lys Glu Lys Leu Gln Glu Gln Arg
             155                 160

Asp Leu Glu Gln Arg Lys Ala Asp Thr Lys
             165                 170

Lys Asn Leu Glu Arg Lys Lys Glu His Gly
             175                 180

Asp Val Leu Ala Glu Asp Leu Tyr Gly Arg
             185                 190

Leu Glu Ile Pro Ala Ile Glu Leu Pro Ser
             195                 200

Glu Asn Glu Arg Gly Tyr Tyr Ile Pro His
             205                 210

Gln Ser Ser Leu Pro Gln Asp Asn Arg Gly
             215                 220

Asn Ser Arg Asp Ser Lys Glu Ile Ser Ile
             225                 230

Ile Glu Lys Thr Asn Arg Glu Ser Ile Thr
             235                 240

Thr Asn Val Glu Gly Arg Arg Asp Ile His
             245                 250

Lys Gly His Leu Glu Glu Lys Lys Asp Gly
             255                 260

Ser Ile Lys Pro Glu Gln Lys Glu Asp Lys
             265                 270

Ser Ala Asp Ile Gln Asn His Thr Leu Glu
             275                 280

Thr Val Asn Ile Ser Asp Val Asn Asp Phe
             285                 290

Gln Ile Ser Lys Tyr Glu Asp Glu Ile Ser
             295                 300

Ala Glu Tyr Asp Asp Ser Leu Ile Asp Glu
             305                 310

Glu Glu Asp Asp Glu Asp Leu Asp Glu Phe
             315                 320

Lys Pro Ile Val Gln Tyr Asp Asn Phe Gln
             325                 330

Asp Glu Glu Asn Ile Gly Ile Tyr Lys Glu
             335                 340

Leu Glu Asp Leu Ile Glu Lys Asn Glu Asn
             345                 350

Leu Asp Asp Leu Asp Glu Gly Ile Glu Lys
             355                 360
```

```
Ser Ser Glu Glu Leu Ser Glu Lys Ile
            365             370

Lys Lys Gly Lys Lys Tyr Glu Lys Thr Lys
            375             380

Asp Asn Asn Phe Lys Pro Asn Asp Lys Ser
            385             390

Leu Tyr Asp Glu His Ile Lys Lys Tyr Lys
            395             400

Asn Asp Lys Gln Val Asn Lys Glu Lys Glu
            405             410

Lys Phe Ile Lys Ser Leu Phe His Ile Phe
            415             420

Asp Gly Asp Asn Glu Ile Leu Gln Ile Val
            425             430

Asp Glu Leu Ser Glu Asp Ile Thr Lys Tyr
            435             440

Phe Met Lys Leu Gly Gly Ser Gly Ser Pro
            445             450

His His His His His His
            455

<210> SEQ ID NO 27
<211> LENGTH: 9
<212> TYPE: PRT
<213> ORGANISM: Artificial sequence
<220> FEATURE:
<223> OTHER INFORMATION: derived LSA-1 peptide PL910

<400> SEQUENCE: 27

Val Ser Gln Thr Asn Phe Lys Ser Leu
                5

<210> SEQ ID NO 28
<211> LENGTH: 8
<212> TYPE: PRT
<213> ORGANISM: Artificial sequence
<220> FEATURE:
<223> OTHER INFORMATION: derived LSA-1 peptide PL911

<400> SEQUENCE: 28

Ser Gln Thr Asn Phe Lys Ser Leu
                5
```

EXPRESSION, PURIFICATION AND USES OF A *PLASMODIUM FALCIPARUM* LIVER STAGE ANTIGEN 1 POLYPEPTIDE

This application claims the benefit for priority under 35 U.S.C. §119(e) from Provisional Application Ser. No. 60/425,719 filed on Nov. 12, 2002.

INTRODUCTION

*Plasmodium falciparum* is the leading cause of malaria morbidity and mortality. The World Health Organization estimates that approximately 200 million cases of malaria are reported yearly, with 3 million deaths (World Health Organization, 1997, Wkly. Epidemiol. Rec. 72:269-276). Although, in the past, efforts have been made to develop effective controls against the mosquito vector using aggressive applications of pesticides, these efforts ultimately led to the development of pesticide resistance. Similarly, efforts at treatment of the disease through anti-parasitic drugs led to parasite drug-resistance. As the anti-vector and anti-parasite approaches failed, efforts became focused on malaria vaccine development as an effective and inexpensive alternative approach.

However, the complex parasitic life cycle has further confounded the efforts to develop efficacious vaccines for malaria. The parasite's life cycle is divided between the mosquito-insect host and the human host. While in the human host, it passes through several developmental stages in different organellar environments, i.e. the liver stage and the red blood stage. Although conceptually simple, in reality the problems that must be considered when designing subunit vaccines for malaria are great. Antigen diversity is a characteristic that must be taken into account and includes a high degree of developmental stage specificity, antigenic variation and antigen polymorphism.

The observation that sterile immunity to malaria can be induced by immunization with irradiated sporozoites (Clyde et al., 1973, J. Med. Sci. 266: 169-277; Krzych et al. 1995, J. Immunol. 155, 4072-4077; Hoffman et al., 2002 JID 185, 1155-1164) has focused attention on the sporozoite and liver stages of the parasite life-cycle as potential targets of an effective vaccine. Liver stage antigen 1 (LSA-1) is a prime candidate for development as a vaccine as it is expressed during the hepatic stage of infection. It is known that peptides or recombinant fragments of the LSA-1 protein elicit specific humoral, cellular and cytokine immune responses from cultured peripheral blood mononuclear cells (PBMC) taken from malaria exposed individuals. These immune responses are correlated with a reduction or absence of parasitemia and falciparum malaria disease in subsequent transmission seasons (Kurtis et al. 2001, Trends in *Parasitology*. 17, 219-223). The *P. falciparum* LSA-1 protein is found within the parasitophorous vacuole (PV), a space defined as that region between the inner plasmalemma and the outer parasitophorous vacuole membrane (PVM). The (PV)forms a distinct ring separating the parasite cytoplasm from the host hepatocyte (Fidock et al., 1994, J. Immunol. 153, 190-204). The PVM is of host origin and is formed by invagination of the host cellular membrane when the parasite invaded the host cell. The LSA-1 protein is approximately 230 kDa in mass. Its expression begins shortly after sporozoite invasion of the liver and increases with liver stage development. It is described as a flocculent material within the parasitophorous vacuole and may also adhere to the surface of merozoites, suggesting a crucial role in liver schizogony perhaps protecting the merozoite surface (Hollingdale et al., 1990, Immunol. Lett. 25, 71-76). When the hepatocyte ruptures, it releases the merozoites encased in LSA-1 protein into the liver sinusoid and into the blood stream (Terzakis et al., 1979, J. Protozool. 26, 385-389).

The LSA-1 protein is characterized by a large central repeat region consisting of about eighty-six 17 amino acid tandem repeats flanked by short non-repetitive N-terminal and C-terminal regions which are highly conserved across strains. Studies have revealed the protein is a target of B-cells (Guerin-Marchand et al. 1987, Nature 329, 164-167; Fidock, et al., 1994, supra; Luty et al., 1998, Eur. Cytokine Netw. 9, 639-646), helper T-cells (Doolan and Hoffman, 2000, J. Immun. 165, 1453-1462; Fidock et al. 1994, supra; Connelly et al., 1997, Infect. Immun. 65, 5082-5087, Luty et al., 1998, supra; Kurtis et al., 1999, supra) and MHC-restricted CD8+ CTLs (Hill et al., 1991, Nature 532, 595-600; Aidoo et al., 1995; Doolan and Hoffman, 2000, J. Immunol. 165, 1453-1462). T-cell epitopes have been defined amongst the amino acid residues in the N-terminal and C-terminal flanking regions and in the central repeat region (Doolan and Hoffman, 2000, J. Immun. 165, 1453-1462, 2000; Kryzch et al., 1995, J. Immunol. 155, 4072-4077; Hill et al., 1991, supra; Fidock et al., 1994, supra). Even though LSA-1 is one of the most immuno-epidemilogically studied *P. falciparum* malaria antigens a vaccine using the protein has not yet been developed.

The *P. falciparum* lsa-1 gene sequences have been used for over a decade in an attempt to make a DNA vaccine against *P. falciparum*. NYVAC-Pf7, a multivalent poxvirus vector made by WRAIR and Virogenetics, contained an lsa-1 gene that encoded a repeatless protein. The NMRC MuStDO5 (a mixture of DNA plasmids constructs encoding part or all of five *P. falciparum* genes: CS, SSP2, LSA-1, EBA-175 and MSP-1), and more recently CSLAM (a mixture of DNA plasmid vaccine constructs encoding all or parts of five *P. falciparum* malaria genes: CS, SSP2, LSA-1, AMA-1 and MSP-1) contain LSA-1 gene sequences in their vaccines. The Oxford University scientists have modified vaccinia Ankara (MVA) and cowpox constructs containing DNA sequences that code for several LSA-1 T-cell epitopes. NMRC is currently constructing alpha-virus (VEE replicons) and adenovirus constructs that contain lsa-1 genes.

All these potential vaccines use LSA-1 gene constructs designed as injectable DNA sequences that will be transcribed and translated in the human host, for example in a DNA plasmid, poxvirus, adenovirus, etc. The researchers have used LSA-1 DNA sequences that express the protein in the immunized host rather then injection of isolated LSA-1 protein s because the LSA-1 protein has proven to be impossible to obtain. It has been very difficult or impossible to express in bacteria, yeast or baculovirus. Therefore recombinant expression and isolation of the protein at a scale that is commercially viable for vaccine development and use has never been achieved.

We have overcome this problem and now can express the protein in bacteria. The expressed product can be isolated and purified to high homogeneity for use as an immunogen or a vaccine.

SUMMARY OF THE INVENTION

The aim of the present invention is to develop a *P. falciparum* liver-stage directed vaccine that will result in lower parasite burden in the human host. To that aim, large-scale expression, purification and characterization of a *P. falciparum* LSA-1 (PfLSA1) immunogenic peptide is necessary. The LSA-1 native protein is about 230 kDa in size and contains a large central segment made up of highly conserved tandem 17 amino acid repeat units. The 3D7 clone of *P. falciparum* contains 86 repeats. The amino acid sequences of the N-terminal and C-terminal portions of the molecule are highly conserved in different isolates examined (Fidock, et al, 1994, supra).

We have designed an LSA-1 polypeptide, LSA-NRC, containing a number of T-cell and B-cell epitopes. Our gene construct contains codons for only the N-terminal (#28-154 residues), the C-terminal (#1630-1909 residues) and two 17 amino acid residue repeats (residue numbers refer to Genbank protein sequence for *P. falciparum*, ID #A45592). We chose to include one copy of the major 17 amino acid repeat, GluGlnGlnSerAspLeuGluGlnGlu-ArgLeuAlaLysGluLysLeuGln (SEQ ID NO:1) that occurs 31 times in the *P. falciparum* 3D7 clone LSA-1 protein, and one copy of a minor repeat GluGlnGlnArgAspLeuGluGlnGlu-ArgLeuAlaLysGluLysLeuGln (SEQ ID NO:2) that occurs 4 times in 3D7 clone protein. These regions have been found to contain T-cell epitopes, including those identified as being associated with immune responses in man (T1, J, LSA-Ter, 1s6, T3, T5, 1s8), and several B-cell epitopes, including the two central repeat regions.

The extreme AT richness of the *P. falciparum* lsa-1 gene makes over-expression in most cell types other than the parasite precarious due to the unusual codon usage. Two codon modification approaches were undertaken to improve the protein yield by genetically re-engineering the gene sequence to introduce nonsynonymous mutations (changes in the nucleic acid sequence that still encode the same amino acid) in order to improve translation rates.

In the first approach, the constructs were designed by substituting frequently used *E. coli* synonymous codons, for the infrequently used codons specified by the *P. falciparum* gene, referred to as 'codon optimization'. In this approach, the same *E. coli* codon is used every time a given amino acid is specified (e.g. CGG for every arginine).

In the second approach, the constructs were designed to "harmonize" translation rates, as predicted by comparison of codon frequency tables between *P. falciparum* and *E. coli*, in an attempt to mimic native translation and proper protein folding. More specifically, the frequency of occurance of each codon in the *P. falciparum* gene was calculated and replaced with an *E. coli* codon with a similar frequency for the same amino acid. Please see U.S. application of Angov et al., Ser. No. 10/440,668, filed on 1 Apr. 2003, for more information on "harmonization". An example of each approach is shown in Table 1.

TABLE 1

| Original *P. falciparum* Codons | Usage rate of original codons in *P. falciparum* | *E. coli* abundance optimized | Codon Usage rate of lsa-nrc$^e$ in *E. coli* | Harmonized lsa-nrc$^h$ codons | Codon Usage rate of lsa-nrc$^h$ in *E. coli* |
|---|---|---|---|---|---|
| AAC | 0.14 | AAC | 0.94 | AAT | 0.06 |
| TTG | 0.14 | CTG | 0.83 | CTC | 0.07 |
| AGA | 0.59 | CGT | 0.74 | CGC | 0.25 |

Two constructs were designed with these approaches in mind. A gene construct, lsa-nrc$^e$, was designed based on the optimized codon usage of the highly expressed genes in *E. coli* cells. Transforming various *E. coli* cell lines with this construct allowed expression of soluble protein. However, cryopreserved, transformed cells were genetically unstable and failed to express LSA-NRC(E) protein after cryopreservation. Additionally, induction of expression of LSA-NRC (E) polypeptide resulted in complete plasmid loss and cell death. The apparent toxicity associated with lsa-nrc$^e$ gene expression and our inability to store transformed cells, made these constructs impractical for vaccine production.

In the second approach, a DNA gene construct, lsa-nrc$^h$ was designed by harmonized codon usage. Transforming various *E. coli* cell lines with this plasmid allowed expression of a soluble protein, and cyropreserved transformed cells were genetically stable and expressed the recombinant LSA-NRC(H) polypeptide. Sequencing of the resulting protein or polypeptide revealed that an insertion of one amino acid was present in the T5 epitope of the recombinant protein. This protein was then referred to as LSA-NRC(H)Mut and is described in the Examples below. We are presently removing the inserted amino acid in order to express a LSA-NRC(H) polypeptide product without the insertion.

We have developed a three column chromatographic purification scheme that results in an LSA-NRC(H) product that is >99% pure. Briefly, the bacterial cells are cracked with a microfluidizer and incubated with low levels of sarkosyl, a detergent to facilitate the removal of endotoxin. The lysate is passed over Ni-NTA and bound material is washed with a buffer with high salt and low pH before elution with imidazole. The product is further purified using DEAE and SP-Sepharose ion exchange chromatographic procedures. The final amount of purified protein obtained is approximately 5 g/Kg of starting bacterial paste.

Balb/c mice have been immunized with LSA-NRC(H)Mut polypeptide emulsified in Montanide ISA-720 adjuvant. The mice responded to the protein by making IgG antibodies indicating that the polypeptide was immunogenic (FIG. 4). These antibodies recognize in vitro cultured liver cells infected with *P. falciparum* 3D7 parasites (FIG. 8) indicating that the antibodies made can recognize the LSA-1 protein in its native structure.

Therefore, it is an object of the present invention to provide a recombinant *P. falciparum* LSA-NRC polypeptide for stimulation of antibody production and T-cell immune responses upon vaccination of individuals and for use in diagnostic assays. When expressed in a host, the *P. falciparum* codon usage is preferably harmonized to the host codon usage, at which point, the expressed product is referred to as an LSA-NRC(H) polypeptide. The exemplified LSA-NRC(H)Mut recombinant polypeptide is harmonized for expression in *E. coli* and consists of the harmonized N-terminal, C-terminal and two tandem 17 amino acid repeats of the LSA-1 protein of *P. falciparum* in addition to an amino acid insertion in the T5 *P. falciparum* epitope. The LSA-NRC (H)Mut polypeptide also includes a 6×His tag on the C-terminal end of the polypeptide for aid in purification of the polypeptide. The nucleotide sequence of the lsa-nrc$^{hmut}$ is specified in SEQ ID NO:3 and the encoded amino acid sequence is specified in SEQ ID NO:4.

Variations of LSA-NRC include peptides with repeats from 0 to 90 wherein the repeats contain conserved amino acids of the same basic 17 amino acids following the order:

$X_1$GlnGln$X_2$Asp$X_3$GluGln$X_4$Arg$X_5$Ala$X_6$Glu$X_7$LeuGln (SEQ ID NO:5) where $x_1$ is either Glu or Gly; $x_2$ is Ser or Arg; $x_3$ is Asp or Ser; $x_4$ is Glu or Asp; $x_5$ is Leu or Arg; $x_6$ is Lys or Asn and $x_7$ is Lys or Thr or Arg. The repeat unit of 17 amino acids can start at any of the amino acids in the 17 amino acid unit, much like the start of a circle can have many points. However, because of the alpha-helical, coiled-coil nature of the tertiary structure of the repeats each unit should maintain the basic ordering of the amino acids.

Similarly, LSA-NRC peptides could also contain less or more of the N-terminal region of LSA-1, extending from the first methionine at residue #1 to around residue #158, and/or more or less of the C-terminal region of LSA-1, extending from approximately amino acid residue #1630-1909, keeping in mind that these regions contain T-cell epitopes which aid in mounting an immune response. The defined epitopes in these regions, shown in Table 2, can be included or excluded, rendered functional, i.e. recognized by an epitope defining-antibody, or nonfunctional, not recognized by an epitope-defining antibody, depending on the intended purpose of the resulting expressed peptide or polypeptide. The N- and C-terminal regions can additionally be presented, whether complete or partial, in multiples of 1 in order to achieve a desired immune response. In addition, insertions, deletions or substitutions can be designed to enhance immunogenicity or reduce immunogenicity of one or more epitopes. As is described in the Examples below, we have designed LSA-NRC(H)Mut wherein the T5 epitope is interrupted by an insertion of one amino acid, an arginine (please see Table 2, SEQ ID NO:15 for the amino acid sequence of the mutant T5 epitope) and have found that the resulting polypeptide is immunogenic.

TABLE 2

Most Common Studied Epitopes of P. falciparum LSA-1

| Epitope Name | Inclusive Amino Acid Numbers | Sequence | References |
|---|---|---|---|
| T1 | 84-107 | LeuThrMetSerAsnValLysAsnValSerGlnThr AsnPheLysSerLeuLeuArgAsnLeuGlyValSer (SEQ ID NO:6) | Krzych, 1995; Connelly, 1997 |
| LSA-Rep | — | GluGlnGlnSerAspLeuGluGlnGluArgLeuAla LysGluLysLeuGln (SEQ ID NO:7) | Fidock, 1994; Jurgen 2001 |
| J | 1613-1636 | GluArgLeuAlaLysGluLysLeuGlnGluGlnGln ArgAspLeuGluGln (SEQ ID NO:8) | Fidock, 1994; Jurgen 2001 |
| NR | 1633-1659 | ThrLysLysAsnLeuGluArgLysLysGluHisGly AspValLeuAlaGluAspLeuTyr (SEQ ID NO: 9) | Fidock, 1994; Jurgen 2001 |
| LSA-Ter | 1686-1719 | AsnSerArgAspSerLysGluIleSerIleIleGlu LysThrAsnArgGluSerIleThrThrAsnValGlu GlyArgArgAspIleHisLysGlyHisLeu (SEQ ID NO:10) | Fidock, 1994; Jurgen 2001 |
| ls6 | 1786-1794 | LysProIleValGlnTyrAspAsnPhe (SEQ ID NO:11) | Hill, 1992 |
| T3 | 1813-1835 | AsnGluAsnLeuAspAspLeuAspGluGlyIleGlu LysSerSerGluGluLeuSerGluGluLysIle (SEQ ID NO:12) | Krzych, 1995; Connelly, 1997 |
| ls8 | 1850-1856 | LysProAsnAspLysSerLeu (SEQ ID NO:13) | Hill, 1992 |
| T5 | 1888-1909 | AspAsnGluIleLeuGlnIleValAspGluLeuSer GluAspIleThrLysTyrPheMetLysLeu (SEQ ID NO:14) | Krzych, 1995; Connelly, 1997 |
| T5-MUtR | 1888-1909 | AspAsnGluIleLeuGlnIleValAspGluArgLeu SerGlueAspIleThrLysTyrPheMetLysLeu (SEQ ID NO:15) | Hillier, unpublished |
| LSA1.1 | 84-104 | LeuThrMetSerAsnValLysAsnValSerGlnThr AsnPheLysSerLeuLeuArgAsnLeuGlyValSer (SEQ ID NO:16) | Joshi, 2000 |
| LSA1.2 | 1742-1760 | HisThrLeuGluThrValAsnIleSerAspValAsn AspPheGlnIleSerLysTyrGlu (SEQ ID NO:17) | Joshi, 2000 |

TABLE 2-continued

Most Common Studied Epitopes of P. falciparum LSA-1

| Epitope Name | Inclusive Amino Acid Numbers | Sequence | References |
|---|---|---|---|
| LSA1.3 | 1779-1796 | AspGluAspLeuAspGluPheLysProIleValGln TyrAspAsnPheGlnAsp (SEQ ID NO:18) | Joshi, 2000 |
| LSA1.4 | 1797-1816 | IleGlyIleTyrLysGluLeuGluAspLeuIleGlu Lys (SEQ ID NO:19) | Joshi, 2000 |
| LSA1.5 | 1817-1834 | AsnGluAsnLeuAspAspLeuAspGluGlyIleGlu LysSerSerGluGluLeuSerGluGluLysIle (SEQ ID NO:20) | Joshi, 2000 |
| LSA1.6 | 1835-1849 | IleLysLysGlyLysLysTyrGluLysThrLysAsp AsnAsnPhe (SEQ ID NO:21) | Joshi, 2000 |
| LSA1.7 | 1888-1909 | AspAsnGluIleLeuGlnIleValAspGluLeuSer GluAspIleThrLysTyrPheMetLysLeu (SEQ ID NO:22) | Joshi, 2000 |
| Doolan 1671 | 1671-1679 | TyrTyrIleProHisGlnSerSerLeu (SEQ ID NO:23) | Doolan, unpublished |
| | | Krzych et al., 1995. J. Immunol. 155, 4072-4077 | |
| | | Fidock et al., 1994. J. Immunol. 153, 190-20 | |
| | | Hill, et al, 1992. Nature 360, 434-439 Joshi, et al., 2000. Infect Immun. 68, 141-150 | |
| | | Connelly et al., 1997. Infect Immun. 65, 5082-5087 | |
| | | Jurgen, et al. , 2001. JID. 183, 168-172 | |

The LSA-NRC polypeptide could optionally include the signal sequence contained in the first 28 residues of the native protein, and/or any other amino acid sequence found in other strains or clones of the *P. falciparum* lsa-1 gene.

When designing the LSA-NRC polypeptide, the epitopes or fragments of the lsa-1 gene chosen may be linked in tandem, N-terminal to C-terminal, in random or fixed order by their ends or cross linked by chemical means by their amino acids.

It is another object of the present invention to provide compositions comprising purified recombinant *P. falciparum* LSA-NRC polypeptide.

It is yet another object of the present invention to provide novel vector constructs for recombinantly expressing *P. falciparum* lsa-nrc, as well as host cells transformed with said vector.

It is also an object of the present invention to provide a method for producing and purifying recombinant *P. falciparum* LSA-NRC polypeptide comprising:

growing a host cell containing a vector expressing *P. falciparum* LSA-NRC polypeptides in a suitable culture medium, causing expression of said vector sequence as defined above under suitable conditions for production of soluble polypeptide and, lysing said transformed host cells and recovering said LSA-NRC polypeptide such that it is essentially free of host toxins.

It is also an object of the present invention to provide diagnostic and immunogenic uses of the recombinant *P. falciparum* LSA-NRC polypeptide of the present invention, as well as to provide kits for diagnostic assays for example in malaria screening and confirmatory antibody tests.

It is also an object of the present invention to provide monoclonal or polyclonal antibodies directed against LSA-NRC which also react with LSA-1, more particularly human monoclonal antibodies or mouse monoclonal antibodies which are humanized, which react specifically with native LSA-1 epitopes, either comprised in peptides or conformational epitopes present in the native parasite or in recombinantly expressed proteins.

It is also an object of the present invention to provide possible uses of anti-LSA-NRC monoclonal antibodies for malaria antigen detection or for therapy to prevent malaria reinfection.

It is yet another object of the present invention to provide a malaria vaccine or an immunogenic composition comprising LSA-NRC of the present invention, in an amount effective to elicit an immune response in an animal or human against *P. falciparum*; and a pharmaceutically acceptable diluent, carrier, or excipient.

It is another object of the present invention to provide a method for eliciting in a subject an immune response against malaria, the method comprising administering to a subject a composition comprising LSA-NRC of the present invention.

The vaccine according to the present invention is inherently safe, is not painful to administer, and should not result in adverse side effects to the vaccinated individual.

All the objects of the present invention are considered to have been met by the embodiments as set out below.

BRIEF DESCRIPTION OF THE DRAWINGS

FIG. 1. Protein gel showing purification of LSA-NRC(H) Mut after three column chromatographic purification.

FIG. 9. Antibodies from malaria infected people recognize LSA-NRC(H)Mut.

DETAILED DESCRIPTION

Figure 2:
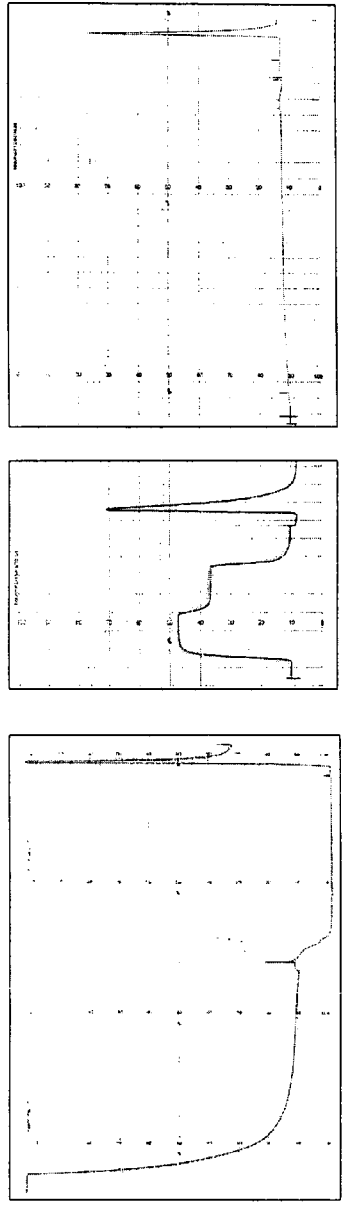
FIG. 2. Purification profiles of LSA-NRC(H)Mut protein after each of the chromatography steps used in purification. The profile is a chart recording tracing of the OD absorbance of the column effluent at 280 nm.

In the description that follows, a number of terms used in recombinant DNA, parasitology and immunology are extensively utilized. In order to provide a clearer and consistent understanding of the specification and claims, including the scope to be given such terms, the following definitions are provided.

In general, an 'epitope' is defined as a linear array of 3-20 amino acids aligned along the surface of a protein. In a linear epitope, the amino acids are joined sequentially and follow the primary structure of the protein. In a conformational epitope, residues are not joined sequentially, but lie linearly along the surface due to the conformation (folding) of the protein. With respect to conformational epitopes, the length of the epitope-defining sequence can be subject to wide variations. The portions of the primary structure of the antigen between the residues defining the epitope may not be critical to the structure of the conformational epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homo-oligomer or hetero-oligomer. As used herein, 'epitope' or 'antigenic determinant' means an amino acid sequence that is immunoreactive. As used herein, an epitope of a designated polypeptide denotes epitopes with the same amino acid sequence as the epitope in the designated polypeptide, and immunologic equivalents thereof. Such equivalents also include strain, subtype (=genotype), or type(group)-specific variants, e.g. of the currently known sequences or strains belonging to *Plasmodium* such as 3D7, FVO, Camp, NF54, and T9/96, or any other known or newly defined *Plasmodium* strain.

The term 'solid phase' intends a solid body to which the individual *P. falciparum* antigen is bound covalently or by noncovalent means such as hydrophobic, ionic, or van der Waals association.

The term 'biological sample' intends a fluid or tissue of a mammalian individual (e.g. an anthropoid, a human), reptilian, avian, or any other zoo or farm animal that commonly contains antibodies produced by the individual, more particularly antibodies against malaria. The fluid or tissue may also contain *P. falciparum* antigen. Such components are known in the art and include, without limitation, blood, plasma, serum, urine, spinal fluid, lymph fluid, secretions of the respiratory, intestinal or genitourinary tracts, tears, saliva, milk, white blood cells and myelomas. Body components include biological liquids. The term 'biological fluid' refers to a fluid obtained from an organism.

The term 'immunologically reactive' means that the antigen in question will react specifically with anti-LSA-1 antibodies, present in vitro or in a body component from a malaria infected individual.

The term 'immune complex' intends the combination formed when an antibody binds to an epitope on an antigen.

The term 'LSA-1' as used herein refers to the native protein of *P. falciparum* that contains all the repeats. By LSA-1 is intended LSA-1 from any strain of *P. falciparum*, e.g. 3D7, FVO, Camp, NF54, T9/96, or any other stain.

The term LSA-NRC means the recombinant protein or polypeptide product of the gene lsa-nrc that contains a series of amino acids from the *P. falciparum* native LSA-1 and that comprises an amino acid sequence defining at least one LSA-1 epitope. We have found that it is necessary to alter the nucleotide sequence of lsa-nrc such that codon frequency is harmonized for expression in *E. coli*. It is understood that the nucleotide sequence of the desired lsa-nrc can be altered such that codon frequency is harmonized for expression in any desired host. Alternatively, it may not be necessary to harmonize the codon frequency if the expressed protein levels are satisfactory for the intended purpose of the expressed LSA-NRC.

In one aspect of the invention, the LSA-NRC(H) extends from approximately amino acid (aa)28 to aa 154, continues with two 17 aa tandem repeats and then continues with aa 1630 to 1909 of the full-length protein (NCBI Genbank accession # A45592). As discussed previously, the frequency of amino acid codons of the LSA-1 sequence in the lsa-nrc$^h$ gene construct have been harmonized with the frequency of *E. coli* codons in order to improve expression of the protein in *E. coli* host. It is envisioned that similar codon harmonization can be achieved for enhanced expression of the desired polypeptide in the host of choice.

The choice of epitopes to be included in a LSA-NRC polypeptide to provide immunogenic and nonimmunogenic variations can vary depending on the intended use of the resulting polypeptide. For example, variations of this peptide can include peptides with repeats from 0 to 90 wherein the repeats contain ones of the same basic 17 amino acids following the order:

$X_1$GlnGln$X_2$Asp$X_3$GluGln$X_4$Arq$X_5$Ala$X_6$Glu$X_7$LeuGln (SEQ ID NO:5) where $x_1$ is either Glu or Gly; $x_2$ is Ser or Arg; $x_3$ is Asp or Ser; $x_4$ is Glu or Asp; $x_5$ is Leu or Arg; $x_6$ is Lys or Asn and $x_7$ is Lys or Thr or Arg. The repeat unit of 17 amino acids can start at any of the amino acids in the 17 amino acid unit, much like the start of a circle can have many points. However, because of the alpha-helical, coiled-coil nature of the tertiary structure of the repeats each unit should maintain the basic ordering of the amino acids. For example, the second repeat unit in LSA-NRC(H) starts following the first repeat with aa #9 (Glu) such that the second repeat unit is in order of GluArgLeuAlaLysGluLysLeuGln-GluGlnGlnArgAspLeuGluGln (SEQ ID NO:2) therefore the amino acid sequence between the N-terminal and C-terminal LSA-1 fragments: GluGlnGlnSerAspLeuGluGlnGlu-ArgLeuAlaLysGluLysLeuGln GluArgLeuAlaLysGlu-LysLeuGlnGluGlnGlnArgAspLeuGluGln (SEQ ID NO:24).

Similarly, LSA-NRC polypeptides can also contain less or more of the N-terminal or C-terminal regions of LSA-1 keeping in mind that these regions contain T-cell epitopes which aid in mounting an immune response. The defined epitopes in these regions, shown in Table 2, can be included or excluded, depending on the intended purpose of the resulting expressed peptide or polypeptide. The N- and C-terminal regions can additionally be presented, whether complete or partial, in multiples of 1 in order to achieve a desired immune response. In addition, insertions, deletions or substitutions can be designed to enhance immunogenicity or reduce immunogenicity of one or more epitopes. As is described in the Examples below, we have designed LSA-NRC(H)Mut wherein the T5 epitope is interrupted by an insertion of one amino acid and have found that the resulting polypeptide is immunogenic.

The LSA-NRC polypeptide could optionally contain the signal sequence contained in the first 28 residues of the native protein, and/or any other amino acid sequence found in other strains or clones of the *P. falciparum* lsa-1 gene.

The LSA-NRC as used herein also includes analogs and truncated forms of LSA-NRC that are immunologically cross-reactive with natural LSA-1.

The term 'homo-oligomer' as used herein refers to a complex of LSA-NRC containing more than one LSA-NRC monomer, e.g. LSA-NRC/LSA-NRC dimers, trimers or tetramers, or any higher-order homo-oligomers of LSA-NRC are all homo-oligomers within the scope of this definition. The oligomers may contain one, two, or several different monomers of LSA-NRC obtained from the sequence of one strain of *P. falciparum* or mixed oligomers from different strains of *Plasmodium falciparum* including for example 3D7, NF-54, T9/96, Camp, FVO, and others. Such mixed oligomers are still homo-oligomers within the scope of this invention, and may allow more universal diagnosis, prophylaxis or treatment of malaria. The homo-oligomers may be linked in tandem, head to tail, in random or fixed order by their ends or cross linked by chemical means by their internal amino acids. Particularly they may be cross-linked by their glutamine (Gln) amino acids by the action of transglutaminase.

The term 'purified' as applied to proteins herein refers to a composition wherein the desired polypeptide comprises at least 35% of the total protein component in the composition. The desired polypeptide preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of the percentage purity as used herein. An 'isolated' LSA-NRC protein intends a *Plasmodium* protein composition that is at least 35% pure.

The term 'essentially purified proteins or polypeptides' refers to proteins purified such that they can be used for in vitro diagnostic methods and as a prophylactic compound. These proteins are substantially free from cellular proteins, vector-derived proteins or other *Plasmodium* components. The proteins of the present invention are purified to homogeneity, at least 80% pure, preferably, 90%, more preferably 95%, more preferably 97%, more preferably 98%, more preferably 99%, even more preferably 99.5%.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces. Schizosaccharomyces, Kluveromyces, Pichia* (e.g. *Pichia pastoris*), *Hansenula* (e.g. *Hansenula polymorpha, Yarowia, Schwaniomyces, Schizosaccharomyces, Zygosaccharomyces* and the like. *Saccharomyces cerevisiae, S. carlsberoensis* and *K. lactis* are the most commonly used yeast hosts, and are convenient fungal hosts.

The term 'prokaryotes' refers to hosts such as *E. coli, Lactobacillus, Lactococcus, Salmonella, Streptococcus, Bacillus subtilis* or *Streptomyces*. Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term 'recombinant polynucleotide or nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence that is comprised of consensus sequences that allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

An 'open reading frame' (ORF) is a region of a polynucleotide sequence which encodes a polypeptide and does not contain stop codons; this region may represent a portion of a coding sequence or a total coding sequence.

A 'coding sequence' is a polynucleotide sequence that is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against malaria, whether partial or complete. A vaccine may also be useful for treatment of an infected individual, in which case it is called a therapeutic vaccine.

The term 'therapeutic' refers to a composition capable of treating malaria infection such that disease symptoms are reduced.

The term 'effective amount' for a therapeutic or prophylactic treatment refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of LSA-NRC for prophylaxis of malaria disease are about 0.01 to 1000 ug/dose, more preferably about 0.1 to 100 ug/dose most preferably about 10-50 ug/dose. Several doses may be needed per individual in order to achieve a sufficient immune response and subsequent protection against malaria.

More particularly, the present invention contemplates essentially purified LSA-NRC and a method for isolating or purifying recombinant LSA-NRC protein.

The term 'LSA-NRC' refers to a polypeptide or an analogue thereof (e.g. mimotopes) comprising an amino acid sequence (and/or amino acid analogues) defining at least one LSA-1 epitope. Typically, the sequences defining the epitope correspond to the amino acid sequence of LSA-1 region of *P. falciparum* (either identically, by harmonization, or via substitution of analogues of the native amino acid residue that do not destroy the epitope). The LSA-NRC(H) protein or polypeptide corresponds to a nucleotide sequence identified in SEQ ID NO:25 and an amino acid sequence identified in SEQ ID NO:26 which spans from amino acid 28-154 of the N-terminal region, two 17 aa repeats of the 86 possible from the full length molecule, and the C-terminal region amino acids #1630-1909 of LSA-1 3D7 allele. Upon expression in *E. coli* LSA-NRC(H) is expected to have an approximate molecular weight of 53 kDa as determined by SDS-PAGE.

The LSA-NRC antigen used in the present invention preferably contains a fragment containing at least one complete epitope, or a substantially full-length version, i.e. containing functional fragments thereof (e.g. fragments which are not missing sequence essential to the formation or retention of an epitope). Furthermore, the polypeptide antigen of the present invention can also include other sequences that do not block or prevent the formation of the epitope of interest. The presence or absence of a epitope can be readily determined through screening the antigen of interest with an antibody as described in the Examples below (polyclonal serum or monoclonal to the conformational epitope).

The LSA-NRC polypeptide antigen of the present invention can be made by any recombinant method that provides the epitope of interest. For example, recombinant expression in *E. coli* is a preferred method to provide non-glycosylated antigens in 'native' conformation. This is most desirable because natural *P. falciparum* antigens are not glycosylated. Proteins secreted from mammalian cells may contain modifications including galactose or sialic acids which may be undesirable for certain diagnostic or vaccine applications. However, it may also be possible and sufficient for certain applications, as it is known for proteins, to express the antigen in other recombinant hosts such as baculovirus and yeast or higher eukaryotes, as long as glycosylation is inhibited.

The polypeptides according to the present invention may be secreted or expressed within compartments of the cell. Preferably, however, the polypeptides of the present invention are expressed within the cell and are released upon lysing the cells.

It is also understood that the isolates used in the examples section of the present invention were not intended to limit the scope of the invention and that an equivalent sequence from a *P. falciparum* isolate from another allele, e.g. FVO, T9/96 or CAMP, can be used to produce a recombinant LSA-1 protein using the methods described in the present application. Other new strains or clones of *P. falciparum* may be a suitable source of LSA-1 sequence for the practice of the present invention.

The LSA-NRC nucleotide sequence of the present invention can be part of a recombinant vector. Therefore, the present invention relates more particularly to the lsa-nrc$^{hmut}$ nucleic acid sequence (SEQ ID NO:3) in recombinant vector, pET KLSA-NRC$^{hmut}$. The LSA-1 genomic sequence was cloned into the base vector pETK(−) a modified pET32 plasmid vector from Novagen (Madison, Wis.). This plasmid comprises, in sequence, a T7 promoter, optionally a lac operator, a ribosome binding site, restriction sites to allow insertion of the structural gene and a T7 terminator sequence. To aid in purification of the expressed protein, a single histidine tag is cloned at the C-terminus. The ampicillin antibiotic resistance gene has been replaced with a kanamycin resistance gene in pETK(−) and the orientation of the kanamycin ORF is opposite to that of the ORF for the gene that is inserted for expression. Examples of other plasmids which contain the T7 inducible promoter include the expression plasmids pET-17b, pET-11a, pET-24a-d(+), and pEt-9a, all from Novagen (Madison, Wis.); see the Novagen catalogue.

The present invention also contemplates host cells transformed with a recombinant vector as defined above. In a preferred embodiment, *E. coli* strain Tuner(DE3), or alternatively BL21 (DE3) (F-ompT hsdSB(rB-mB-) gal dcm (DE3) is employed. The above plasmids may be transformed into this strain or other strains of *E. coli* having the following characteristics: a T7 RNA polymerase rec gene, lon, ompT protease mutants or any other *E. coli* with a protease deficiency such as *E. coli* origami. Preferably, the host includes Tuner(DE3) and any of its precursors. Other host cells such as insect cells can be used taking into account that other cells may result in lower levels of expression.

Eukaryotic hosts include lower and higher eukaryotic hosts as described in the definitions section. Lower eukaryotic hosts include yeast cells well known in the art. Higher eukaryotic hosts mainly include mammalian cell lines known in the art and include many immortalized cell lines available from the ATCC, including HeLa cells, Chinese hamster ovary (CHO) cells, Baby hamster kidney (BHK) cells, PK15, RK13 and a number of other cell lines. LSA-NRC expressed in these cells will be glycosylated unless the cells have been altered such that glycosylation of the recombinant protein is not possible. It is expected that when producing LSA-NRC in a eukaryotic expression system, extensive investigation into methods for expressing, isolating, purifying, and characterizing the protein would be required as eukaryotic cells post-translationally modify this protein and this would alter protein structure and immunogenicity.

Methods for introducing vectors into cells are known in the art. Please see e.g., Maniatis, Fitsch and Sambrook, *Molecular Cloning; A Laboratory* Manual (1982) or *DNA Cloning*, Volumes I and II (D. N. Glover ed. 1985) for general cloning methods.

A preferred method for isolating or purifying LSA-NRC as defined above is further characterized as comprising at least the following steps:

(i) growing a host cell as defined above transformed with a recombinant vector expressing LSA-NRC proteins in a suitable culture medium, (ii) causing expression of said vector sequence as defined above under suitable conditions for production of a soluble polypeptide, (iii) lysing said transformed host cells and recovering said LSA-NRC polypeptide such that it retains its native conformation and is essentially pure.

Once the host has been transformed with the vector, the transformed cells are grown in culture in the presence of the desired antibiotic. For FDA regulatory purposes, it is preferable to use tetracycline or kanamycin. When cells reach optimal biomass density, in this case about 0.7-0.9 OD 600, in small culture flasks or 7-100D 600 in bulk fermentors, the cells are induced to produce the recombinant protein, preferably, with dioxin free IPTG. IPTG allows expression of T7 polymerase protein from the *E. coli* (DE3) host cell chromosome, which acts on the T7 promoter on the expression plasmid. The concentration of inducer, i.e. IPTG, added affects the maximal protein synthesis. It was found that a concentration of 0.5 mM IPTG was best, however, a range of 0.25 to 1.0 mM would be sufficient to produce 80-100% of maximal.

The cells are then collected and lysed to release the recombinant polypeptide. Preferably, lysis is with a microfluidizer, however a French Press or other mechanical breakage devise would work; alternatively cells could be lysed by chemical means using urea, guanidine-HCL or detergents such as sarkosyl. Lysed cells are centrifuged to pellet cellular debris, for example at 10,000 rpm for 30 min, and the supernatant is removed and incubated with low levels, 0.1% to 5%, of sarkosyl, a detergent, to facilitate the removal of endotoxin. Lysis is preferably at a temperature of about 0° C.-15° C., more preferably about 5-10° C. A high salt concentration of about 1.0-2.0 M is preferable. Salts used include NaCl or other monovalent ions.

Preferably, the *E. coli* endotoxin is separated and removed from the recombinant polypeptide. This can be done several ways. For LSA-NRC(H)Mut, a large majority of the endotoxin was removed by applying the bacterial lysate directly to a Ni$^{+2}$-NTA column, which bound the LSA-NRC(H)Mut protein. Endotoxin, and other *E. coli* proteins, carbohydrates and lipopolysaccharides were washed off the column by washing the resin with a buffer of low pH, about 5.7 to 6.1, preferably about pH 5.9 and containing high salt, preferably about 2 M NaCl. The cell paste to resin ratio can be about 1:8 to about 1:12 w/v, preferably about 1:10 w/v. The recombinant protein can be eluted by addition of a higher pH buffer of about 6.5 to about 7.5, preferably about pH 7.0, in a phosphate buffer of about 10-30 mM, more preferably about 20 mM sodium phosphate buffer and 300 mM-500 mM imidazole, preferably 400 mM.

At this point the recombinant protein is about 80% pure. If further purity is required, ion-exchange chromatography can be implemented e.g. DEAE and SP-Sepharose. The column is preferably with an ionic character such that the pH used will not promote endotoxin and nucleic acid binding at the concentration of salt, about 260-300 mM, preferably 280 mM, utilized to elute the protein. LSA-NRC(H)Mut was subjected to DEAE Sepharose ion exchange chromatography. The pH of the buffer can be about 6.5 to about 7.5, preferably about 7.0.

Finally, the eluted sample (about 0.1 mg/ml, can be subjected to further ion exchange chromatography for further concentration and purification. The LSA-NRC(H)Mut was subjected to SP-Sepharose ion exchange chromatography. The pH of the buffer can be about 6.5 to about 7.5, preferably about 7.0. The salt concentration is about 130 mM to about 170 mM, preferably about 150 mM.

The present invention also relates to a composition comprising peptides or polypeptides as described above, for in vitro detection of malaria antibodies present in a biological sample. Therefore, the present invention also relates to an LSA-1 specific antibody raised upon immunizing an animal with a LSA-NRC peptide or protein composition, with said antibody being specifically reactive with LSA-1 or LSA-NRC or any of the polypeptides or peptides as defined above, and with said antibody being preferably a monoclonal antibody.

The present invention also relates to an LSA-NRC specific antibody screened from a variable chain library in plasmids or phages or from a population of human B-cells by means of a process known in the art, with said antibody being reactive with any of the polypeptides or peptides as defined above, and with said antibody being preferably a monoclonal antibody.

The LSA-NRC specific monoclonal antibodies of the invention can be produced by any hybridoma liable to be formed according to classical methods from splenic or lymph node cells of an animal, particularly from a mouse or rat, immunized against the *Plasmodium* polypeptides or peptides according to the invention, as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labeled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains from cDNA or genomic clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with malaria, or vaccinated against malaria. Such human monoclonal antibodies are prepared, for instance, by means of human peripheral blood lymphocytes (PBL) repopulation of severe combined immune deficiency (SCID) mice, or by means of transgenic mice in which human immunoglobulin genes have been used to replace the mouse genes.

The invention also relates to the use of the proteins or peptides of the invention, for the selection of recombinant antibodies by the process of repertoire cloning.

Antibodies directed to peptides or single or specific proteins derived from a certain strain may be used as a medicament, more particularly for incorporation into an immunoassay for the detection of *Plasmodium* strains for detecting the presence of LSA-1 antigens, or antigens containing LSA-NRC epitopes, for prognosing/monitoring of malaria disease, or as therapeutic agents.

Alternatively, the present invention also relates to the use of any of the above-specified LSA-NRC monoclonal antibodies for the preparation of an immunoassay kit for detecting the presence of LSA-1 antigen or LSA-NRC antigens containing LSA-1 epitopes in a biological samples for the preparation of a kit for prognosing/monitoring of malaria disease or for the preparation of a malaria medicament.

The present invention also relates to a method for in vitro diagnosis or detection of malaria antigen present in a biological sample, comprising at least the following steps:

(i) contacting said biological sample with any of the LSA-NRC specific monoclonal antibodies as defined above, preferably in an immobilized form under appropriate conditions which allow the formation of an immune complex, (ii) removing unbound components, (iii) incubating the immune complexes formed with heterologous antibodies, which specifically bind to the antibodies present in the sample to be analyzed, with said heterologous antibodies conjugated to a detectable label under appropriate conditions, (iv) detecting the presence of said immune complexes visually or mechanically (e.g. by means of densitometry, fluorimetry, colorimetry).

The present invention also relates to a kit for in vitro diagnosis of a malaria antigen present in a biological sample, comprising:

at least one monoclonal antibody as defined above, with said antibody being preferentially immobilized on a solid substrate, a buffer or components necessary for producing the buffer enabling binding reaction between these antibodies and the malaria antigens present in the biological sample, and a means for detecting the immune complexes formed in the preceding binding reaction.

The kit can possibly also include an automated scanning and interpretation device for inferring the malaria antigens present in the sample from the observed binding pattern.

Monoclonal antibodies according to the present invention are suitable both as therapeutic and prophylactic agents for treating or preventing malaria infection in susceptible malaria-infected subjects.

In general, this will comprise administering a therapeutically or prophylactically effective amount of one or more monoclonal antibodies of the present invention to a susceptible subject or one exhibiting malaria infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before parasite can be controlled, and the induced immune response to the MAbs in the subject does not induce "serum sickness" in the subject. Preferably, the MAbs administered exhibit some secondary functions such as binding to Fc receptors of the subject.

Treatment of individuals having malaria infection may comprise the administration of a therapeutically effective amount of LSA-NRC antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to LSA-1, or an antibody capable of protecting against malaria in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered.

In a similar approach, another prophylactic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-LSA-NRC response (Linthicum, D. S. and Farid, N. R., Anti-Idiotypes, Receptors, and Molecular Mimicry (1988), pp 1-5 and 285-300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies or immunoreactive T-cells against LSA-1 in a manner that has either prophylactical or therapeutical value. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cyteine and derivatives thereof. Alternative protein modification techniques may be used e.g., $NH_2$-acetylation or COOH-terminal amidation, to provide additional means for coupling or fusing the peptide to another protein or peptide molecule or to a support.

The antibodies capable of protecting against malaria are intended to be provided to recipient subjects in an amount sufficient to effect a reduction in the malaria infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

The present invention more particularly relates to a composition comprising at least one of the above-specified peptides or a recombinant LSA-NRC protein or polypeptide composition as defined above, for use as a vaccine for immunizing a mammal, preferably humans, against malaria, comprising administering a sufficient amount of the composition possibly accompanied by pharmaceutically acceptable adjuvant(s), to produce an immune response.

The proteins of the present invention, preferably purified recombinant LSA-NRC from one or more alleles of *P. falciparum*, e.g., T9/96, FVO, 3D7, NF54, or CAMP, are expected to provide a particularly useful vaccine antigen, since the antigen has very little sequence variation in the N-terminal and C-terminal regions that contain the T-cell epitopes.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to: T helper cell type I adjuvant, Montanide, aluminum hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine(nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) and RIBI, which contains three components extracted from bacteria, monophosphoryl lipid A, trehalose dimycolate, and cell wall skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, Mass.) or SAF-1 (Syntex) may be used. Further, Complete Freund's Adjuvant (CFA) and Incomplete Freund's Adjuvant (IFA) may be used for non-human applications and research purposes.

All documents cited herein supra and infra are hereby incorporated by reference thereto.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. The LSA-NRC proteins of the invention may also be incorporated into Immune Stimulating Complexes together with saponins, for example QuilA (IS-COMS).

Immunogenic compositions used as vaccines comprise a 'sufficient amount' or 'an immunologically effective amount' of the proteins of the present invention, as well as any other of the above mentioned components, as needed. 'Immunologically effective amount', means that the administration of that amount to an individual, either in a single dose or as part of a series, is effective for treatment, as defined above. This amount varies depending upon the health and physical condition of the individual to be treated, the taxonomic group of individual to be treated (e.g. nonhuman primate, primate, etc.), the capacity of the individual's immune system to synthesize antibodies, the degree of protection desired, the formulation of the vaccine, the treating doctor's assessment of the medical situation, the strain of malaria infection, and other relevant factors. It is expected that the amount will fall in a relatively broad range that can be determined through routine trials. Usually, the amount will vary from 0.01 to 1000 ug/dose, more particularly from about 1.0 to 100 ug/dose most preferably from about 10 to 50 ug/dose.

The proteins may also serve as vaccine carriers to present homologous (e.g. other malaria antigens, such as EBA-175 or AMA-1) or heterologous (non-malaria) antigens. In this use, the proteins of the invention provide an immunogenic carrier capable of stimulating an immune response to other antigens.

For example, the polypeptide can be included in a composition containing other *P. falciparum* malaria proteins including RTS, S (Stoute et al., 1998. J. Infect. Dis. 178(4):1139-44), AMA-1 (Dutta et al., 2002 Infect Immun. 70(6): 3101-10), MSP-1 (Angov, et al. 2003. Mol Biochem Parasitol. 128:195-204), or *P. vivax* malaria proteins like MSP-1 (Dutta, et al. 2001. Infect Immun 69, 5464-5470) or DBP (Dutta et al, 2000. Mol BioChem Para. 109/2; 179-85). The *P. falciparum* LSA-NRC polypeptide could also provide immune help or boosting to other vaccine constructs that might contain *P. falciparum* LSA-NRC epitopes. These other vaccine constructs could be of protein (e.g. a synthetic or recombinant amino acid construct containing LSA-1 sequences), nucleic acid (e.g. naked DNA plasmid vector containing LSA-1 gene fragments) or live viral (e.g. poxvirus, adenovirus or VEE virus genetically engineered to contain LSA-1 DNA sequences) or bacterial (e.g. *Salmonella* or *Mycobacterium* cells containing extra chromosomal plasmids or chromosomally integrated DNA sequences of LSA-1) vectors in origin such that they are delivered to the intended host as a DNA sequence that would be translated into a polypeptide that contain sequences similar to, or contained in, the LSA-NRC polypeptide. The *P. falciparum* LSA-NRC polypeptide could also provide immune help in a vaccine by being in the first, second or third priming injections that are followed by another vaccine construct (booster injection) that would contain *P. falciparum* LSA-NRC epitopes. The booster injection could also be the *P. falciparum* LSA-NRC polypeptide in a different adjuvant than it was emulsified in or combined with for the priming injection or injections.

The antigen may be conjugated either by conventional chemical methods, or may be cloned into the gene encoding LSA-NRC fused to the 5' end or the 3' end of the LSA-NRC gene. The vaccine may be administered in conjunction with other immunoregulatory agents.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the compounds, whether antibodies or vaccines, disclosed herein may be carried out by any suitable means, including parenteral injection (such as intraperitoneal, subcutaneous, or intramuscular injection), orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container means containing the above-described vaccine. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The present invention also relates to a method for in vitro diagnosis of malaria antibodies present in a biological sample, comprising at least the following steps (i) contacting said biological sample with a composition comprising any of the LSA-NRC recombinant protein or peptides as defined above, preferably in an immobilized form under appropriate conditions which allow the formation of an immune complex, wherein said peptide or protein can be a biotinylated peptide or protein which is covalently bound to a solid substrate by means of streptavidin or avidin complexes, (ii) removing unbound components, (iii) incubating the immune complexes formed with heterologous antibodies, with said heterologous antibodies having conjugated to a detectable label under appropriate conditions, (iv) detecting the presence of said immune complexes visually or mechanically (e.g. by means of densitometry, fluorimetry, colorimetry).

The present invention also relates to a kit for determining the presence of malaria antibodies, in a biological sample, comprising:

(i) at least one peptide or protein composition as defined above, possibly in combination with other polypeptides or peptides from *Plasmodium* or other types of malaria parasite, with said peptides or proteins being preferentially immobilized on a solid support, more preferably on different microwells of the same ELISA plate, and even more preferentially on one and the same membrane strip, (ii) a buffer or components necessary for producing the buffer enabling binding reaction between these polypeptides or peptides and the antibodies against malaria present in the biological sample, (iii) means for detecting the immune complexes formed in the preceding binding reaction, (iv) possibly also including an automated scanning and interpretation device for inferring the malaria parasite present in the sample from the observed binding pattern.

The immunoassay methods according to the present invention utilize LSA-NRC domains that maintain linear and conformational epitopes recognized by antibodies in the sera from individuals infected with a malaria parasite. The LSA-NRC antigens of the present invention may be employed in virtually any assay format that employs a known antigen to detect antibodies. A common feature of all of these assays is that the antigen is contacted with the body component suspected of containing malaria antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen and antibody.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon.™.), diazotized paper, nylon membranes, activated beads, and Protein A beads. For example, Dynatech Immunolon.™.1 or Immunlon.™. 2 micrometer plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are known in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of malaria antibodies in the antibody-antigen complexes is directly monitored. This may be accomplished by determining whether labeled anti-xenogeneic (e.g. anti-human) antibodies which recognize an epitope on anti-malaria antibodies will bind due to complex formation. In a competitive format, the amount of malaria antibodies in the sample is deduced by monitoring the competitive effect on the binding of a known amount of labeled antibody (or other competing ligand) in the complex.

Complexes formed comprising anti-malaria antibody (or in the case of competitive assays, the amount of competing antibody) are detected by any of a number of known techniques, depending on the format. For example, unlabeled malaria antibodies in the complex may be detected using a conjugate of anti-xenogeneic Ig complexed with a label (e.g. an enzyme label).

In an immunoprecipitation or agglutination assay format the reaction between the malaria antigens and the antibody forms a network that precipitates from the solution or suspension and forms a visible layer or film of precipitate. If no anti-malaria antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles. However, gelatin particles may also be used. The assays utilizing either of these carriers are based on passive agglutination of the particles coated with purified antigens.

The LSA-NRC proteins, polypeptides, or antigens of the present invention will typically be packaged in the form of a kit for use in these immunoassays. The kit will normally contain in separate containers the LSA-NRC antigen, control antibody formulations (positive and/or negative), labeled antibody when the assay format requires the same and signal generating reagents (e.g. enzyme substrate) if the label does not generate a signal directly. The LSA-NRC antigen may be already bound to a solid matrix or separate with reagents for binding it to the matrix. Instructions (e.g. written, tape, CD-ROM, etc.) for carrying out the assay usually will be included in the kit.

Immunoassays that utilize the LSA-NRC antigen are useful in screening blood for the preparation of a supply from which potentially infective malaria parasite is lacking. The method for the preparation of the blood supply comprises the following steps. Reacting a body component, preferably blood or a blood component, from the individual donating blood with LSA-NRC proteins of the present invention to allow an immunological reaction between malaria antibodies, if any, and the LSA-NRC antigen. Detecting whether anti-malaria antibody—LSA-NRC antigen complexes are formed as a result of the reacting. Blood contributed to the blood supply is from donors that do not exhibit antibodies to the native LSA-NRC antigens.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following Materials and Methods were used in the Examples below.

Cloning and Expression.

Two gene constructs containing modified codons to encode for the N-terminal (#28-154 residues), the C-terminal (#1630-1909 residues) and two 17 amino acid repeats of LSA-1 of the *P. falciparum* 3D7 clone (residue numbers refer to Genbank protein sequence for 3D7 clone, ID #A45592) were commercially synthesized (Retrogen, San Diego, Calif.). The first gene construct (lsa-nrc$^e$) was designed based on the codon usage of the highly expressed genes in *E. coli* cells and the second gene construct (lsa-nrc$^h$) was designed to "harmonize" translation rates, as predicted by comparison of codon frequency tables between *P. falciparum* and *E. coli* (Angov et al, U.S. patent application Ser. No. 10/440,668 filed on 1 Apr. 2003). We chose one copy of the major 17 amino acid repeats, GluGlnGlnSerAspLeuGluGlnGlu-ArgLeuAlaLysGluLysLeuGln, (SEQ ID NO:1) that occurs 31 times in 3D7 clone protein and one copy of a minor repeat, GluGlnGlnArgAspLeuGluGlnGlu-ArgLeuAlaLysGluLysLeuGln (SEQ ID NO:2), that occurs 4 times in 3D7 clone protein. The synthetic genes were ligated into the Nde I, Not I sites of the modified pET32 plasmid pET K—. The resultant plasmid construct was designated pET KLSA-NRC$^e$ or pET KLSA-NRC$^h$ (later referred to as pET KLSA-NRC$^{hmut}$) and each recombinant plasmid was transformed into *E. coli* DH5α cells. The insert was sequenced on both strands of DNA. For protein expression the plasmid was transformed into an *E. coli* host strain Tuner (DE3) (Novagen, Madison, Wis.). The transformations were plated onto LB Agar plates with 50 pg/ml kanamycin. The pET KLSA-NRC$^e$ was unstable in Tuner (DE3) cells as well as Bl21(DE3), HMS174(DE3). Protein expression was low and plasmids could not be maintained more than several passages. However the pET KLSA-NRC$^{hmut}$ plasmid was stable and expression of LSA-NRC(H)Mut polypeptide was good. The expression of LSA-NRC(H)Mut was confirmed by IPTG induction in shake flask cultures and cell banks were prepared by inoculating LB supplemented with 1% glucose and 35 μg/ml kanamycin. Cultures were grown to an OD 600=1 and cryopreserved in 8% glycerol and were used to prepare the inocula for bulk fermentation.

Fermentation

The expression of LSA-NRC(H)Mut was performed in a 10-liter bioreactor (New Brunswick Scientific, Edison, N.J.) at the lab scale and in a 300-liter bioreactor (New Brunswick Scientific) at the WRAIR Department of Biologics Research, Pilot Production Facility. To prepare *E. coli* cell paste containing LSA-NRC(H)Mut Select APS Super broth medium containing 35 μg/ml kanamycin and 1% glucose was inoculated with a fresh stationary phase culture in accordance with BPR-670-00. The culture is grown at 37±1 EC to an optical density of 7-8OD and induced with 0.5 mM IPTG for 2±0.25 hrs. The cell paste is harvested by centrifugation at 15,000 rpm and stored frozen at −80±10° C.

Plasmid Stability

The presence of recombinant plasmid in *E. coli* Tuner (DE3) cells after fermentation was determined by plating an appropriate dilution of cells on LB agar plates containing either kanamycin 50 ug/ml (selective plates) and on LB agar plates containing no antibiotic (non-selective plates). The percent plasmid retention was calculated using colony counts on appropriate dilution plates containing between 30 and 300 colonies.

Metal Affinity Purification

All buffers were maintained at 4±2 EC; all chemicals used during purification were ACS certified or the next best available grade. Purification was carried out at RT on a Waters-600 liquid chromatography system. Cell paste was thawed and suspended in 25 times w/v of Buffer A (50 mM sodium phosphate (NaP), 2 M NaCl, pH 5.9) and mixed until homogenous. This suspension was mixed and the *E. coli* cells were disrupted by high-pressure microfluidization (Model 1109, Microfluidic Corp., Newton, Mass.). The cell lysate was cleared by centrifugation at 10,000×g and Buffer B (20% sodium N-lauroyl sarcosine) (sarkosyl) was added to a final concentration of 0.5% and incubated at 4±2 EC for 30 min before loading onto a Ni$^{+2}$-NTA Superflow column (Qiagen, Valencia, Calif.; 10 ml packed resin per gram paste). The Ni$^{+2}$-NTA column was pre-equilibrated with buffer-C (Buffer A containing 0.5% sarkosyl; pH 5.9). After loading the lysate, the Ni$^{+2}$-NTA resin was washed with 40 column volumes (CV) of Buffer D (Buffer A with 5 mM imidazole, 0.5% sarkosyl; pH 5.9) followed by 40 CV of Buffer E (20 mM NaP, 5 mM imidazole, 75 mM NaCl; pH 7.0). Bound proteins were eluted from the column in Buffer F containing 300 mM imidazole (pH 7.0).

Ion-exchange Purification

Ion-exchange column resins were sanitized with 0.2 N NaOH before use and then equilibrated to initial binding conditions. The protein was concentrated on a DEAE Sepharose anion-exchange column (Amersham Pharmacia Biotech, Piscataway, N.J.; 3 ml packed resin per gram of starting bacterial paste). The column was pre-equilibrated with Buffer G (Buffer F without imidazole). After loading the protein, the column was washed with 10 CV of Buffer H (20 mM NaP, 200 mM NaCl, pH 7.0). LSA-NRC(H)Mut was eluted in buffer-I containing a final concentration of 280 mM NaCl (pH 7.0). LSA-NRC(H)Mut eluted from the DEAE column was diluted to 50 mM NaCl, pH 7.0 and loaded on an SP Sepharose cation-exchange column (Amersham Pharmacia Biotech; 2 ml packed resin per gram paste), pre-equilibrated with buffer-K (20 mM NaP, 50 mM NaCl; pH 7.0). The column was washed with 20 CV of Buffer-K. LSA-NRC(H)Mut was eluted from the column in Buffer L (20 mM NaP, 150 mM NaCl, pH 7.0).

Formulation, Lyophilization and Storage

Purified LSA-NRC(H)Mut protein eluted from the SP column was quantified by Bio-Rad protein assay (BioRad, Richmond, Calif.). LSA-NRC(H)Mut was vialed at 100 μg ml$^{-1}$, 65 μg protein per vial, in the final formulation buffer (23.5 mM NaH$_2$PO$_4$.H$_2$O, 30 mM NaCl, 0.1 mM EDTA, 3.15% sucrose; pH 7.1) and lyophilized.

Residual Sarkosyl and Endotoxin Content Determination

The residual sarkosyl in purified LSA-NRC(H)Mut protein preparation was measured by a reversed-phase HPLC method. Endotoxin content was estimated using the chromogenic *Limulus Amebocyte* Lysate (LAL) kinetic assay (Associates of Cape Cod, Falmouth, Mass.). Dilutions of all protein samples and LAL standard were prepared in pyrogen-free 96 well plates. Positive control solutions prepared for the standard curves ranged from 1 endotoxin unit (EU) ml$^{-1}$ to 0.06 EU ml$^{-1}$, in two-fold serial dilutions. The assay was carried out as per the manufacturer's instructions and the 96-well plates were read at 405 nm on V$_{max}$ kinetic microplate reader at 2 min intervals for 60 min (Molecular Devices Corp., Sunnyvale, Calif.).

Purity and Stability Analysis

LSA-NRC(H)Mut was evaluated for purity on precast polyacrylamide gels (4-12% gradient Bis-Tris, Invitrogen, Carlsbad, Calif.), 0.1-16 µg protein loaded per well. Gels were stained with Coomassie blue or GelCode SilverSNAP stain (Pierce, Rockford, Ill.), destained, scanned on a Laser densitometer and acquired data was analyzed by ImageQuant 5.1 software (Molecular Dynamics, Sunnyvale, Calif.). Residual host cell protein (HCP) content, was assessed by ELISA and Western blotting, using commercially available kits (Cygnus Technologies, Plainville, Mass.). The HCP standard recommended by the manufacturer was used. In addition to this control, a lysate of the *E. coli* host was tested as a standard between 1000 and 15 ng ml$^{-1}$ protein concentration, to determine if the kit was capable of detecting proteins from this specific host *E. coli*. Immunoblotting for HCP determination (Cygnus Technologies kit) was carried out using the HCP standard provided by the manufacturer. The proteins were electrophoretically transferred to a nitrocellulose membrane and the western blot assay was performed as per the manufacturer's instructions. Stability of LSA-NRC was determined by SDS-PAGE and western blotting of protein samples drawn monthly from aliquots stored at $-80°$ C., $-30°$ C., $4°$ C., $22°$ C. (RT) and $37°$ C.

Gel-Permeation (GPC) and Reversed-phase (RPC) Chromatography

HPLC analysis of purified protein was carried out using a Waters-510 HPLC pump, connected to Waters-712 WISP autosampler and controlled by Millenium Release 3.2 chromatographic software (Waters Corp., Milford, Mass.). Waters-996 PDA detector was used to monitor the elution profiles. For GPC analysis a Shodex Protein KW-803 column (Waters Corp., Milford, Mass.) was used with 10 µg protein injection. Buffer system consisted of 20 mM sodium phosphate, 100 mM $K_2SO_4$ (pH 7.15) at 0.5 ml min$^{-1}$ flow rate. The column was calibrated with molecular weight standards (BioRad). RPC analysis was done with a C8 Aquapore RP-300 Å column, 7µ, 30×2.1 mm (PE Brownlee, Norwalk, Conn.) at 0.5 ml min$^{-1}$ flow-rate and 4-12 µg protein per load. Solvent A: 0.05% trifluroacetic acid (TFA) in $H_2O$; solvent B: 0.05% TFA in acetonitrile. The solvent gradient consisted of 100% solvent A for 5 min, 100% to 30% solvent A over 15 min, 30% to 0% solvent A over 5 min and back to 100% solvent A over 5 min.

LSA-NRC(H)Mut Animal Immunizations:

Groups of five Balb/c, C57BL/6 and C57BL/7-TgN (HLA2.1) female mice (male and females for -TgN mice), 8-10 weeks old, were immunized three times with formulations containing 0.1, 1.0 and 10 µg of LSA-NRC(H)Mut and Montanide ISA 720® (Seppic, France) as adjuvant. A group immunized with adjuvant alone was used as control. Each formulation was prepared as a 100 µl/dose and given subcutaneously at 0, 4 and 8 wks. Serum samples were taken two weeks after each immunization and tested for specific LSA-NRC(H)Mut antibodies. One or two mice were randomly selected from each group 7 days after the second immunization and their spleens were removed. Spleen cells harvested, pooled and tested for interferon gamma (IFN-gamma) production as described below.

Rabbit Immunizations

Three NZW rabbits, 3 months old, were immunized subcutaneously three times with 1-ml formulations containing 100 µg LSA-NRC(H)Mut/Montanide ISA 720. Immunizations were given at 0, 4 and 8 wks and serum samples were obtained two weeks after each immunization.

Human Serum

Human serum samples were obtained from adult individuals living in malaria endemic areas in Kenya and from healthy volunteers exposed to irradiated *P. falciparum* sporozoites as part of a vaccine trial (Hoffman et al, 2002, supra.).

ELISA.

Mouse and rabbit sera were screened for specific LSA-NRC(H)Mut antibody production on ELISA. Briefly, 96-well microtiter plates (Dynax, Chantilly, Va.) were coated with 50 ng per well of either LSA-NRC$^H$, incubated overnight at 4° C., blocked for 1 hour with 1×PBS-0.05% Tween 20 (PBST) containing 5% casein (Sigma, St. Louis, Mo.), and washed four times with PBST. Plates were incubated for 1 hr at room temperature, RT, with consecutive dilutions of sera starting at 1:50. The plates were washed four times with PBST and incubated with 1:4000 dilution of anti-mouse or anti-rabbit IgG HRP-conjugated secondary antibody (Southern biotech) for 1 hr, RT. Then they again were washed four times and developed for 30 min with ABTS [2,2'-azinobis(3-ethylbenzthiazolinesulfonic acid)]-peroxidase substrate (Kirkegaard & Perry Laboratories, Gaithersburg, Md.). OD values were obtained using a Titertek® plate reader using a 405 nm filter and included into a computer spreadsheet. Antibody titers were expressed as the serum dilutions that give OD=1.0.

Mouse IgG subclass production was analyzed using a similar assay but replacing the secondary antibody with anti-mouse IgG1, IgG2a, IgG2b or IgG3 HRP-conjugated secondary antibody (Southern biotech)

Western Blot.

LSA-NRC(H)Mut, LSA-1 N term, LSA-1 C-term, AMA-1, TRAP, EBA-175 and AMA-1/E samples at 0.2-0.5 µg/lane were run on 4-12% Bis-Tris (Invitrogen, Carlsbad, Calif.) gel at 150 volts for 45 min, RT, and transferred into nitrocellulose paper filters. The filters were blocked for 1 hr with 1×PBST-5% casein (Sigma, St. Louis, Mo.), and washed four times with PBST. Filters strips containing one lane with LSA-NRC (H)Mut, or several lanes with all the related or unrelated malaria antigens, mentioned above, were incubated with sera from individuals exposed to *P. falciparum* or with sera from immunized animals at 1:200 and 1:500 dilutions. Incubation was allowed for 2 hr at RT then the filter were washed and incubated with the respective anti-IgG AP-conjugated secondary antibody for another hr. Recognition of antigen by serum antibodies was noted after development with a solution containing NBT/BCIP substrate (Roche diagnostics, Indianapolis Ind.).

IFA:

The human hepatoblastoma cell line HC04 was grown on Lab-Tek® slide chambers (Nalge-Nunc, Rochester, N.Y.) and infected with NF54 *P. falciparum* sporozoites. After 7-8 days post-infection, cells were fixed with cold methanol and incubated with preimmune and immune rabbit sera (post-2$^{nd}$ immunization at 1:200) for 45 min at RT. Slides were washed with 1×PBS and incubates during 45 min with goat anti-rabbit IgG FITC-conjugated secondary antibody (Southern biotech, Birmingham, Ala.) at 1:100 dilution. Recognition of native LSA-1 *P. falciparum* protein on infected hepatocytes was visualized using a 492-nm UV microscopy. Preimmune rabbit serum and a mouse monoclonal antibody to the *P. falciparum* HSP-60 protein were used as negative and positive control respectively.

IFN-gamma Production on Mice:

The Interferon-gamma detection module (R&D systems Inc. Minneapolis, Minn.) was used to determine the ex-vivo production of this cytokine in response to LSA-NRC(H)Mut. For this assay, spleen cells from LSA-NRC$^H$ immunized C57BL/6 and C57BL/6 TgN mice, at $2.0 \times 10^5$ cells per well, were cultured in Iscove's modified Dulbecco's medium supplemented with 10% fetal bovine serum (BioWhittaker, Walkersville, Md.), 2 mM L-glutamine, 55 µM 2-mercaptoethanol, 1 mM sodium pyruvate, 0.1 mM nonessential amino acids, and 100 U/ml of penicillin-streptomycin (Invitrogen) at 37° C. under a humidified atmosphere with 5% $CO_2$ for 48 hours. Cultures were done in triplicate in the presence of LSA-NRC(H)Mut, the derived LSA-1 peptides PL910 and PL911 (VSQTNFKSL (SEQ ID NO:27) and SQTNFKSL (SEQ ID NO:28), respectively) at 10 µg/ml or a mixture of both peptides, at 5 µg/ml-each, in 96-well filtration plates (MultiScreen® HA, Millipore, Billerica, Mass.) previously coated with a mouse IFN-gamma capture monoclonal antibody. Cultures done in presence of 10 µg/ml AMA-1/E, 5 µg/ml concanavalin A, or medium alone were used as control. Plates were then washed eight times with 1×PBS and incubated overnight at 4° C. with a mouse IFN-gamma detection/biotinylated monoclonal antibody. Plates were washed eight times and were incubated at RT for 2 hr with a streptavidin-AP conjugate. Plates were washed ten times and developed with NBT/BCIP. ELISPOTS were quantified manually using a dissection microscope.

EXAMPLE 1

We have produced a recombinant product based on the LSA-1 protein from *P. falciparum* 3D7 strain. Using codon harmonization, a novel approach, we have been able to enhance the expression of a gene lsa-nrc$^{hmut}$, that encodes a protein LSA-NRC(H)Mut in *E. coli* Tuner (DE3) strain. The expressed recombinant protein is in soluble form even at high expression levels.

Figure 3:
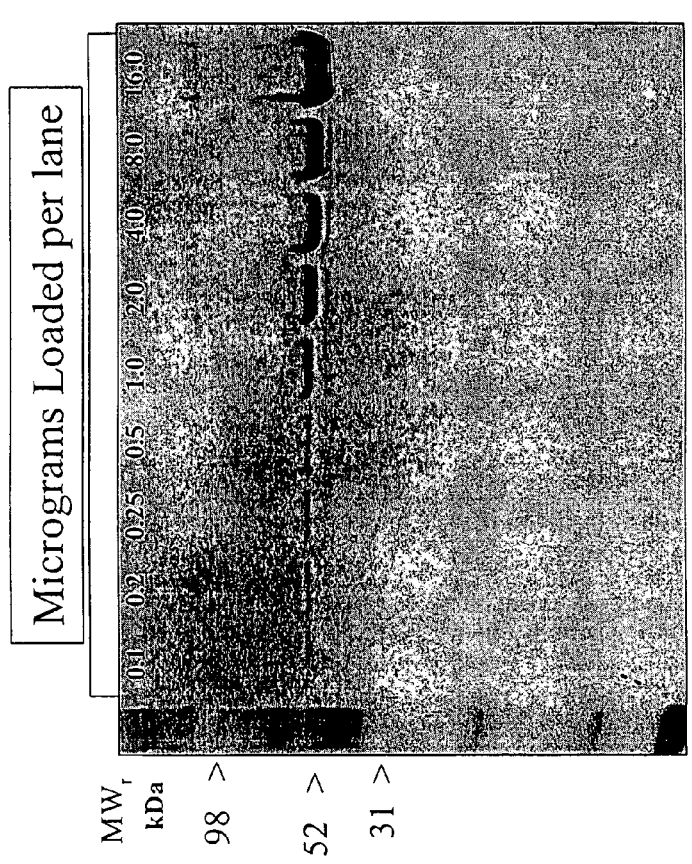
FIG. 3. Silver stained SDS-PAGE gel of final purification product after elution off SP-Sepharose.

We have developed a three column chromatographic purification scheme that results in an LSA-NRC product that is >99% pure (see FIG. 1). The purification profiles of the protein through the steps is shown in FIG. 2. The final amount of purified protein obtained is approximately 5 g/kg of starting bacterial paste. The final purification product was analyzed on an SDS-PAGE gel and silver stained (FIG. 3). The minor band which starts to appear in the 1.0 ug load has been determined, by N-terminal sequencing to be an LSA-NRC (H)Mut product that is the result of a secondary initiation site at the Met at position 62 in the protein. Scans of the gel show that it is less that 10% of the major band. The minor band that appears above the major band starting in load 4.0 ug is a dimmer of LSA-NRC(H)Mut. Host cell protein analysis indicates less than 0.1 ug *E. coli* per 50 ug product (data not shown).

EXAMPLE 2

Figure 4:
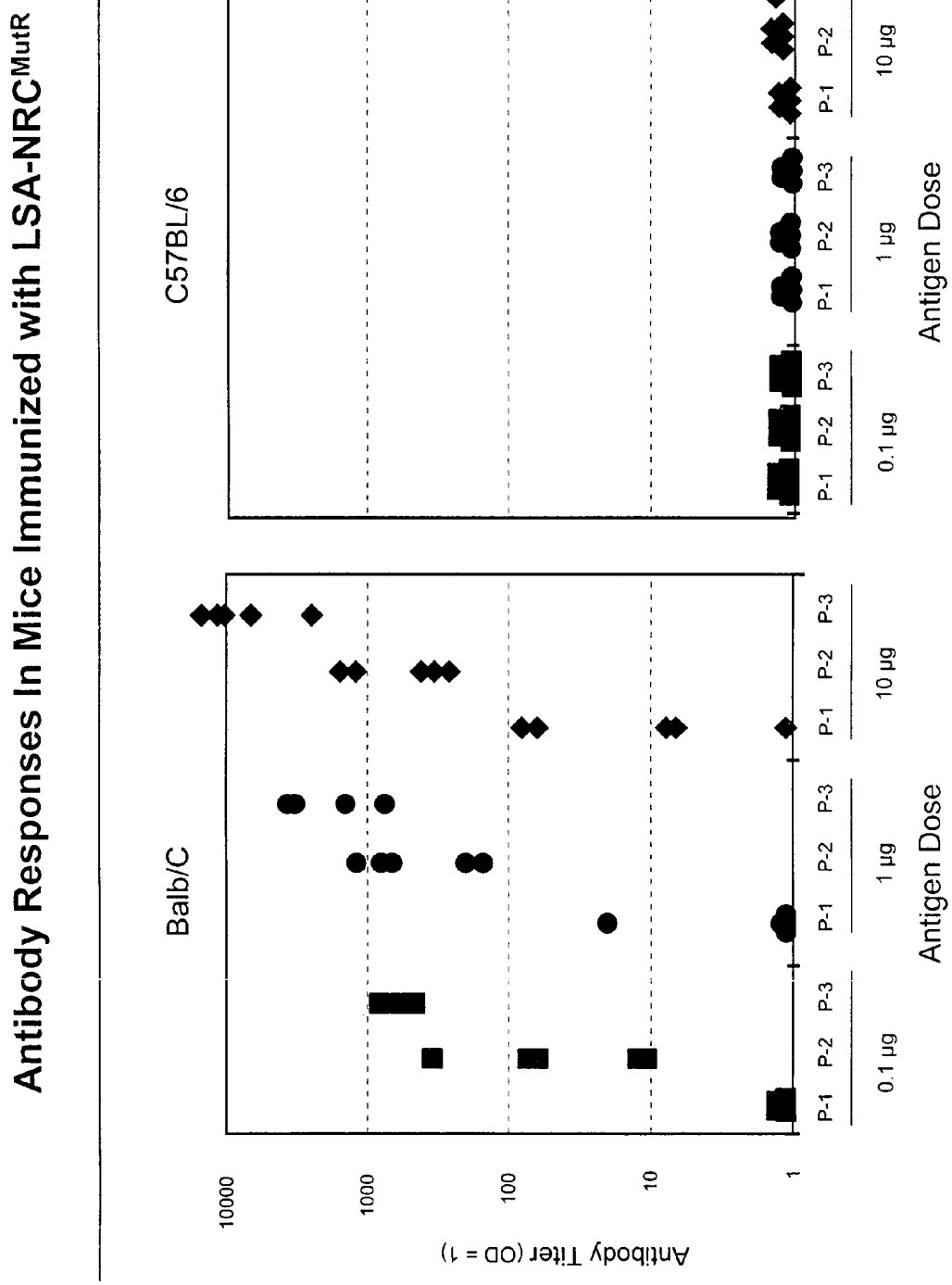
FIG. 4. Development of antibody in two strains of mice, Balb/c and C57BL/6, after immunization with LSA-NRC(H) Mut in Montanide ISA-720 by the subcutaneous route of injection. Each symbol represents the titer of one mouse in that group. P-1, P2 and P3 refer to samples of sera taken two weeks post-1, post-2 and post-3 after immunization with the indicated amount of protein. Balb/C were responders to the polypeptide while c57Bl/6 were generally non-responders.
Figure 5:
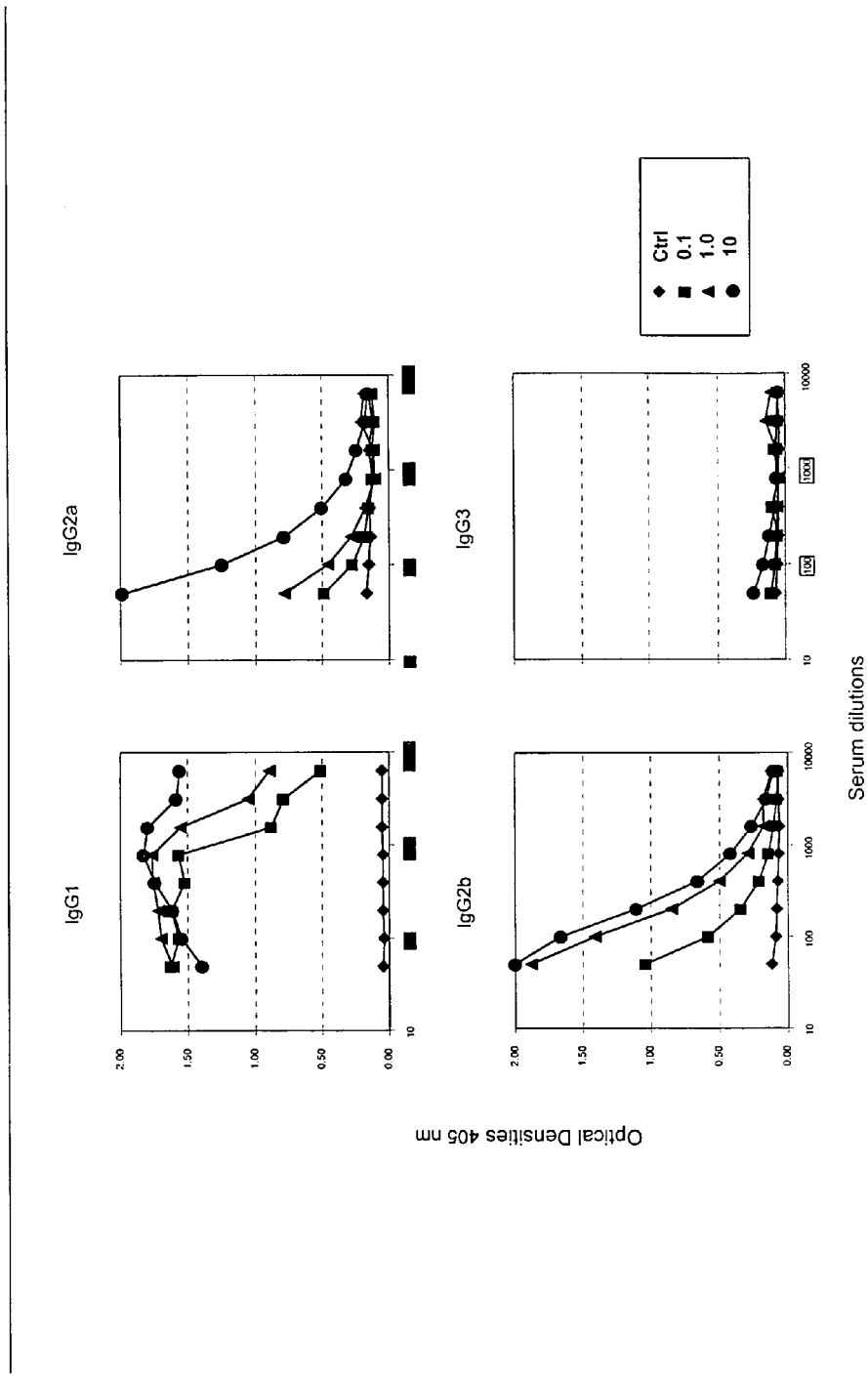
FIG. 5. Isotype of antibody molecules from responder Balb/c mice to LSA-NRC(H)Mut. The major isotype antibody formed in Balb/c mice was IgG1, with some IgG2a and IgG2b formed. Very little IgG3 was made in Balb/C mice in response to LSA-NRC(H)Mut.

Two mouse strains, C57Blk/6 and Balb/c, have been immunized with LSA-NRC(H)Mut protein emulsified in Montanide 720 adjuvant. While the Balb/c mice responded to the protein by making antibodies, the C57Blk/7 mice were nonresponders (FIG. 4). This is similar to observations of Joshi et al. (2000, supra) who showed that C57Blk/6 mice were also non-responders to synthetic peptide epitopes of LSA-1. The major isotype antibody formed in Balb/c mice was IgG1, with some IgG2a and IgG2b formed (FIG. 5). Very little IgG3 was made in Balb/c mice in response to LSA-NRC (H)Mut (FIG. 5).

Figure 7:
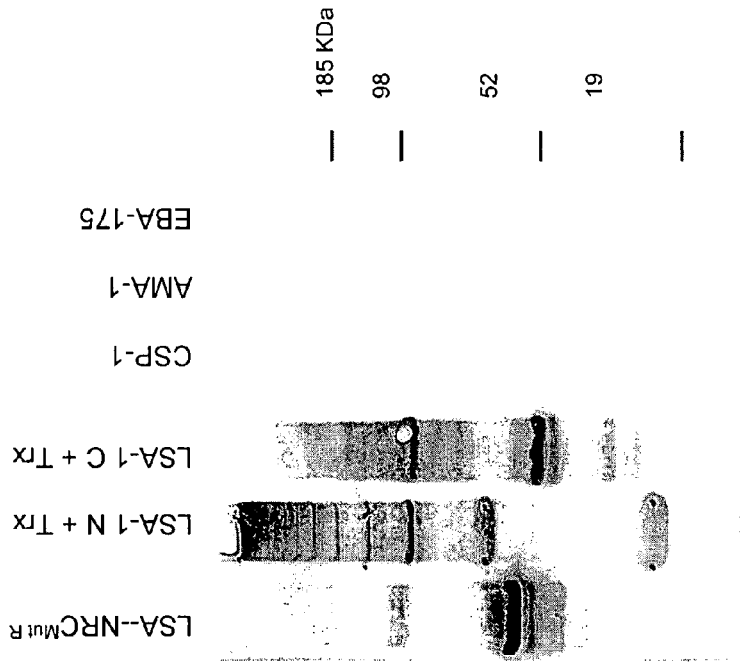
FIG. 7. Rabbits immunized with LSA-NRC(H)Mut make antibodies that recognize the N-terminal and the C-terminal portions of LSA-NRC$^{MutR}$. LSA-1N+trx and LSA-1C+trx are bacterial expressed domains of LSA-1 (Kurtis, et al 2001, supra). CSP is recombinant full length *P. falciparum* circumsporozoite protein; AMA-1 is recombinant ectodomain or *P. falciparum* AMA-1; EBA-175 is recombinant *P. falciparum* EBA-175rII.

Serum from rabbits immunized with LSA-NRC(H)Mut also contained antibodies that recognize the N-terminal and the C-terminal portions of LSA-NRC(H)Mut (FIG. 7). Similarly, a Western blot of human serum obtained from adult individuals living in malaria endemic areas in Kenya shows that antibodies from infected humans recognize LSA-NRC (H)Mut (FIG. 9).

EXAMPLE 3

Figure 6:
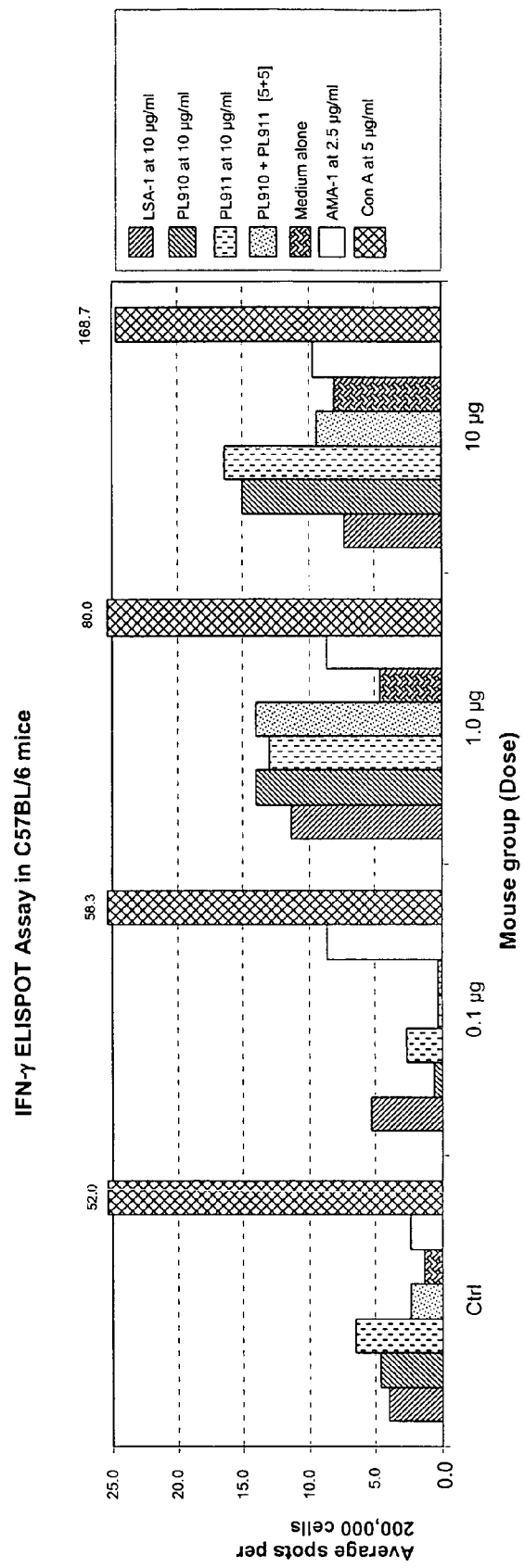
FIG. 6. Interferon-gamma production in C57Bl/6 mice. Spleen cells from mice immunized with LSA-NRC(H)Mut tended to produce IFN-gamma as detected by ELISPOT assay.

The interferon-gamma detection module was used to determine the ex-vivo production of this cytokine in response to LSA-NRC(H)Mut. For this assay, spleen cells from LSA-NRC(H)Mut immunized C57Blk/6 and C57BL/6 TgN mice were cultured in the presence of LSA-NRC(H)Mut on filtration plates previously coated with a mouse IFN-gamma capture monoclonal antibody. After washing, IFN-gamma detection/biotinylated monoclonal antibody was added and ELISPOTS were quantified. Results indicate that spleen cells from mice immunized with LSA-NRC(H)Mut tended to produce IFN-gamma (FIG. 6).

EXAMPLE 4

Figure 8:
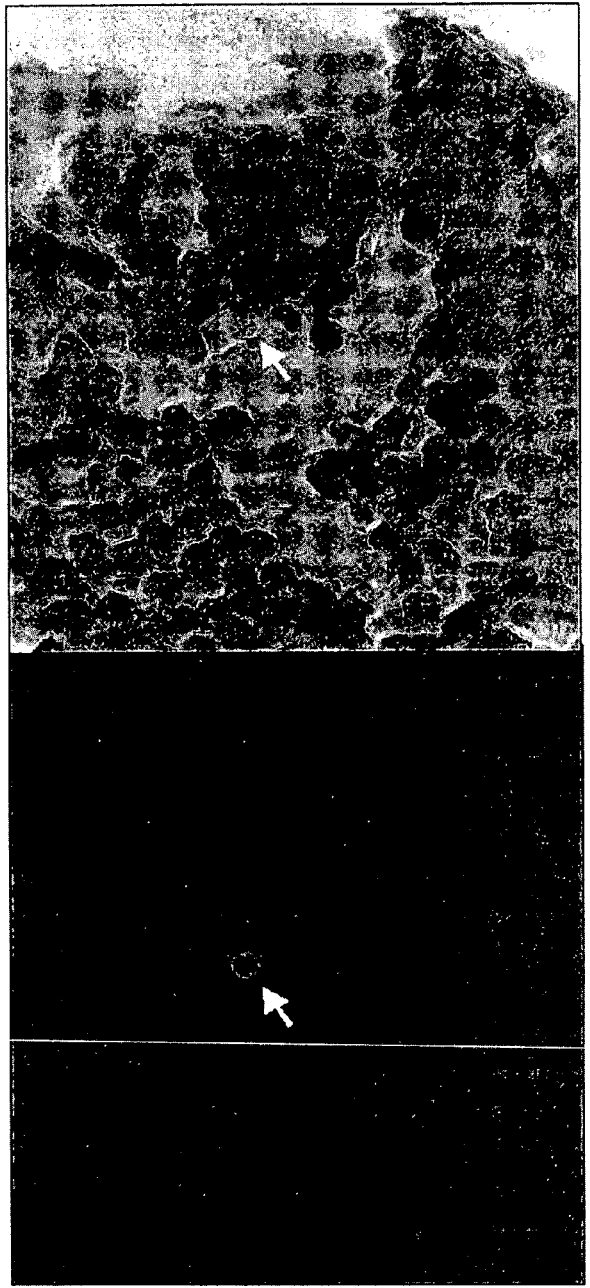
FIG. 8. IFA of infected liver cells in tissue culture. Arrow points to schizont developing in the cell.

Recognition of native LSA-1 *P. falciparum* protein on infected hepatocytes was visualized using a 492-nm UV microscopy using serum from LSA-NRC(H)Mut immunized rabbits. FIG. 8 shows that the immune serum recognized a schizont developing in the infected hepatocyte.

What is claimed is:

1. A purified recombinant polypeptide LSA-NRC(H) specified in SEQ ID NO:26.

2. A composition comprising the recombinant polypeptide of claim 1.

3. A method for producing and purifying recombinant *P. falciparum* LSA-NRC(H) polypeptide of claim 1 comprising:

(i) growing a host cell containing a vector expressing *P. falciparum* LSA-NRC(H) polypeptide of claim 1 in a suitable culture medium, (ii) causing expression of said vector under suitable conditions for production of soluble LSA-NRC(H) polypeptide and, (iii) lysing said host cells and recovering said LSA-NRC (H) polypeptide such that it retains its native folding.

4. The method of claim 3 further comprising removal of *E. coli* endotoxin.

5. The method of claim 4 wherein said removal of endotoxin is by (i) application of the lysed bacteria to a resin containing Ni-NTA and washing said resin bound material with low pH, high salt buffer, (ii) removal of bound material from Ni-NTA resin and binding to other ion affinity resins such as DEAE and SP-Sepharose resins such that the LSA-NRC(H) polypeptide binds and the endotoxins can be washed away.

6. The purified recombinant protein according to claim 1, wherein said purified recombinant protein is at least 90% pure.

7. An immunogenic carrier comprising a polypeptide according to claim 1.

8. A method for in vitro diagnosis of malaria antibodies in a biological sample, comprising
   (i) contacting said biological sample with a composition comprising a LSA-NRC(H) polypeptide according to claim 1 under appropriate conditions which allow the formation of an immune complex, wherein said polypeptide is labeled with a detectable label, and
   (ii) detecting the presence of said immune complexes visually or mechanically.

9. A kit for determining the presence of malaria antibodies in a biological sample, comprising:
   (i) a polypeptide composition according to claim 2, a buffer or components necessary for producing a buffer;
   (ii) means for detecting immune complexes between the polypeptide and antibodies present in the sample.

10. A kit for monitoring malaria infection or prognosing the response to treatment of patients suffering from malaria infection comprising:
   (i) at least one LSA-NRC(H) polypeptide according to claim 1,
   (ii) a buffer or buffer components,
   (iii) means for detecting the immune complexes formed between the polypeptide and antibodies present in the sample.

11. An immunogenic composition comprising the polypeptide according to claim 1.

12. The immunogenic composition of claim 11 further comprising an adjuvant.

13. The immunogenic composition of claim 12 wherein said adjuvant is chosen from the group consisting of: Montanide and alum.

14. A method for inducing in a subject an immune response against malaria infection comprising administering to said subject a composition comprising an immunologically effect amount of *P. falciparum* LSA-NRC(H) of claim 1 in an acceptable diluent.

15. The method of claim 14 wherein said composition further comprises an adjuvant.

16. The method of claim 15 wherein said adjuvant is selected from the group consisting of Montanide, and alum.

17. The polypeptide of claim 1 encoded by the polynucleotide sequence specified in SEQ ID NO:25.

* * * * *